(12) United States Patent
Yuan et al.

(10) Patent No.: US 7,390,836 B2
(45) Date of Patent: Jun. 24, 2008

(54) SMALL MOLECULES USED TO INCREASE CELL DEATH

(75) Inventors: Junying Yuan, Newton, MA (US); Alexei Degterev, Brighton, MA (US); Timothy J. Mitchison, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/606,583

(22) Filed: Nov. 30, 2006

(65) Prior Publication Data

US 2007/0219277 A1  Sep. 20, 2007

Related U.S. Application Data

(62) Division of application No. 10/802,902, filed on Mar. 16, 2004, now Pat. No. 7,144,905, which is a division of application No. 10/196,080, filed on Jul. 16, 2002, now Pat. No. 6,706,766, which is a division of application No. 09/736,502, filed on Dec. 13, 2000, now abandoned.

(60) Provisional application No. 60/170,329, filed on Dec. 13, 1999.

(51) Int. Cl.
A61K 31/167 (2006.01)
(52) U.S. Cl. ........................ 514/617; 514/622
(58) Field of Classification Search ................ 514/617, 514/622
See application file for complete search history.

(56) References Cited

U.S. PATENT DOCUMENTS

| 3,798,258 | A |   | 3/1974 | Patchett et al. |
|---|---|---|---|---|
| 4,791,126 | A |   | 12/1988 | Tanouchi et al. |
| 4,831,045 | A |   | 5/1989 | Tanouchi et al. |
| 4,965,155 | A |   | 10/1990 | Nishiguchi et al. |
| 5,523,314 | A |   | 6/1996 | Bue-Valleskey et al. |
| 5,834,309 | A |   | 11/1998 | Thompson et al. |
| 5,955,593 | A |   | 9/1999 | Korsmeyer |
| 6,706,766 | B2 | * | 3/2004 | Yuan et al. ................ 514/617 |
| 7,144,905 | B2 | * | 12/2006 | Yuan et al. ................ 514/369 |

OTHER PUBLICATIONS

Milanesi et al., "The Mitochondrial Effects of Small Organic Ligands of BCL-2: Sensitization of BCL-2-Overexpressing Cells to Apoptosis by a Pyrimidine-2,4,6-Trione Derivative," J. Biol. Chem. 281:10066-10072 (2006).
Ray et al., "Sensitization of Prostate Carcinoma Cells to Apo2L/TRAIL by a Bcl-2 Family Protein Inhibitor," Apoptosis 10:1411-1418 (2005).
Adams et al., "The Bcl-2 Protein Family: Arbiters of Cell Survival," Science (1998) 281:1322-1326.
Andreasch, STN International HCAPLUS Database, Columbus (Ohio), Accession No. 1911:9676 (1911).
Chittenden et al., "A Conserved Domain in Bak, Distinct From BH1 and BH2, Mediates Cell Death and Protein Binding Functions," EMBO J. (1995) 14:5589-5596.
Clarke et al., "A Recombinant $bcl-x_s$ Adenovirus Selectively Induces Apoptosis in Cancer Cells but Not in Normal Bone Marrow Cells," Proceedings of the National Academy of Sciences USA (1995) 92:11024-11028.
Dandliker et al., "Equilibrium and Kinetic Inhibition Assays Based upon Fluorescence Polarization," Methods in Enzymology (1981) 74:3-28.
Gross et al., "BCL-2 Family Members and the Mitochondria in Apoptosis," Genes & J (1999) 13:1899-1911.
Holinger et al., "Bak BH3 Peptides Antagonize $Bcl-x_L$ Function and Induce Apoptosis through Cytochrome c-independent Activation of Caspases," Journal of Biological Chemistry (1999) 274:13298-13304.
Kelekar et al., "Bcl-2-Family Proteins: the Role of the BH3 Domain in Apoptosis," Trends in Cell Biology (1998) 8:324-330.
Mahajan et al., "Bcl-2 and Bax Interactions in Mitochondria Probed with Green Fluorescent Protein and Fluorescence Resonance Energy Transfer," Nature Biotechnology (1998) 16:547-552.
McDonnell et al., "Solution Structure of the Proapoptotic Molecule BID: A Structural Basis for Apoptotic Agonists and Antagonists," Cell (1999) 96:625-634.
Mikhailitsyn et al., CA (1992)116:235197.
Mikhailitsyn et al., "A Search for New Antiparasitic Agents. 6. Synthesis of Haloidbenzamides Containing Nitrogen-related Benzophenone or Diphenyl Sulfonic Substitute and Study of Their Acute Toxicity," Meditsinskaya Parazitologiya I Parazitamye Bolezni, (1991) 4:43-46.
An English translation of Mikhailitsyn et al., "Search for New Antiparasitic Agents. 6. Synthesis of Haloidbenzamides Containing Nitrogen-related Benzophenone or Diphenyl Sulfonic Substitute and Study of Their Acute Toxicity," Meditsinskaya Parazitologiya I Parazitamye Bolezni, (1991) 4:43-46.
Minn et al., "Recent Progress on the Regulation of Apoptosis by Bcl-2 Family Members," Advances in Immunology (1998) 70:245-279.
Reiter et al., STN International HCAPLUS Database, Columbus (Ohio), Accession No. 1995:380326 (1995).
Roa et al., "Enhancement of radiation sensitivity with BH3I-1 in non-small cell lung cancer," Clin. Invest. Med. (2005) 28:55-63.
Sattler et al., "Structure of $Bcl-x_L$ Bak Peptide Complex: Recognition Between Regulators of Apoptosis," Science (1997) 275:983-986.
Taylor et al., "Induction of Endogenous Bcl-xS through the Control of Bcl-x Pre-mRNA Splicing by Antisense Oligonucleotides," Nature Biotechnology (1999) 17:1097-1100.
Thomadaki and Scorilas, "BCL2 family of apoptosis-related genes: functions and clinical implications in cancer," Crit. Rev. Clin. Lab. Sci. (2006) 43:1-67.

* cited by examiner

Primary Examiner—Golam M. M. Shameem
(74) Attorney, Agent, or Firm—Clark & Elbing LLP; Kristina Bieker-Brady

(57) ABSTRACT

The invention features methods for increasing cell death. The invention also features compounds used to increase cell death. The invention further features methods for identifying compounds that increase cell death.

9 Claims, 14 Drawing Sheets

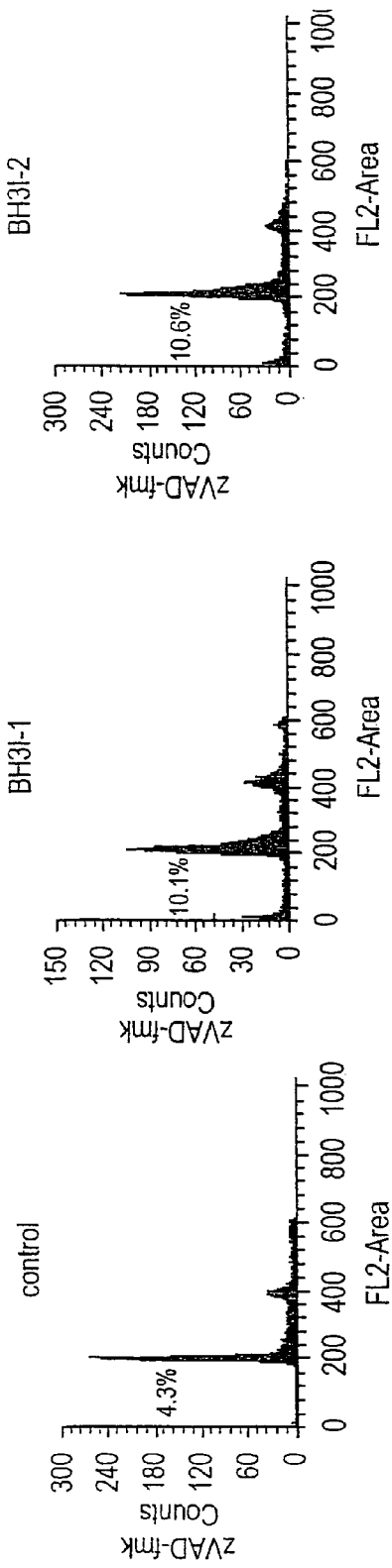
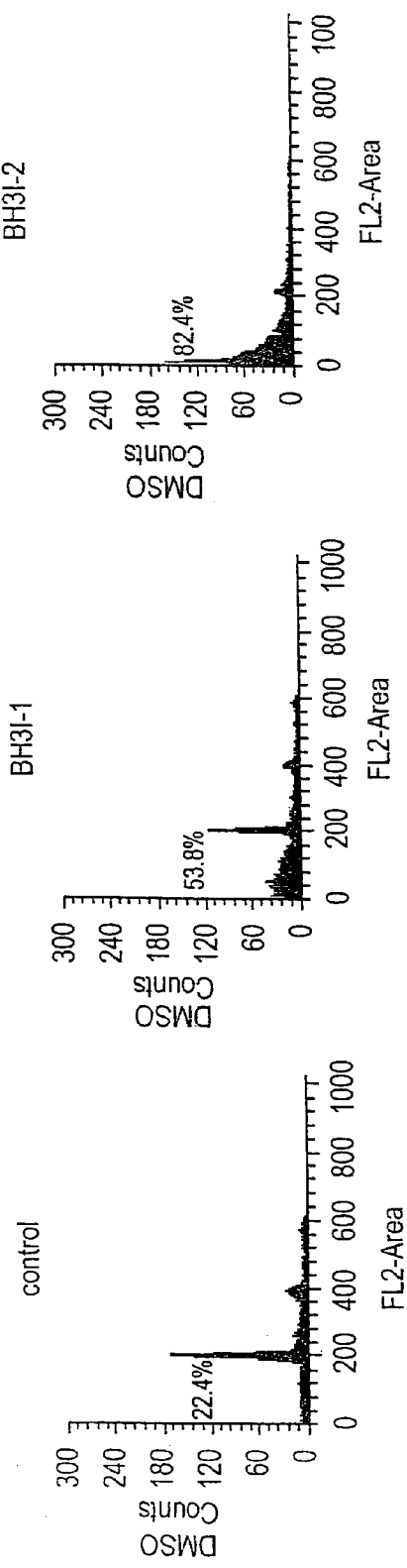
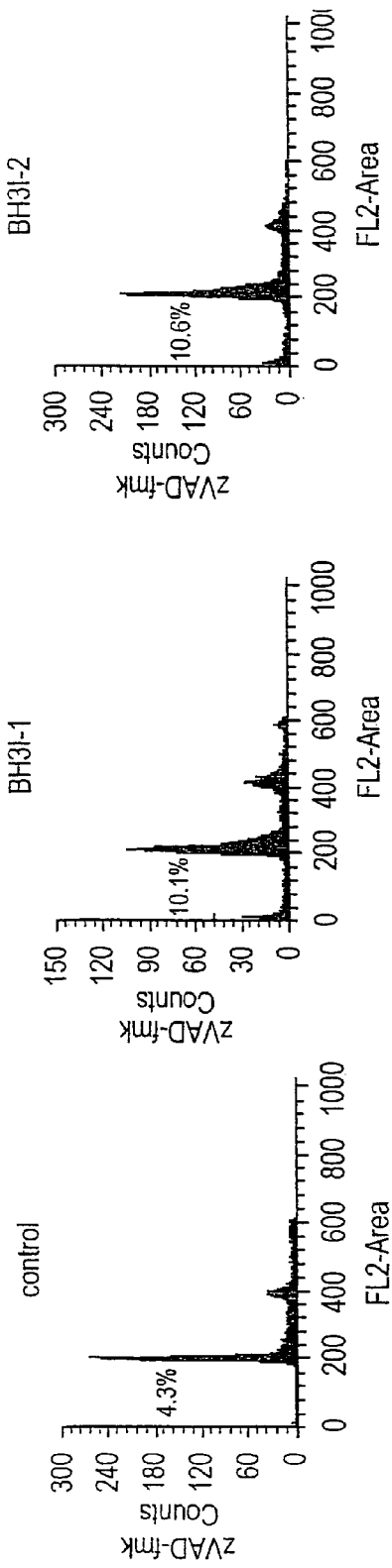
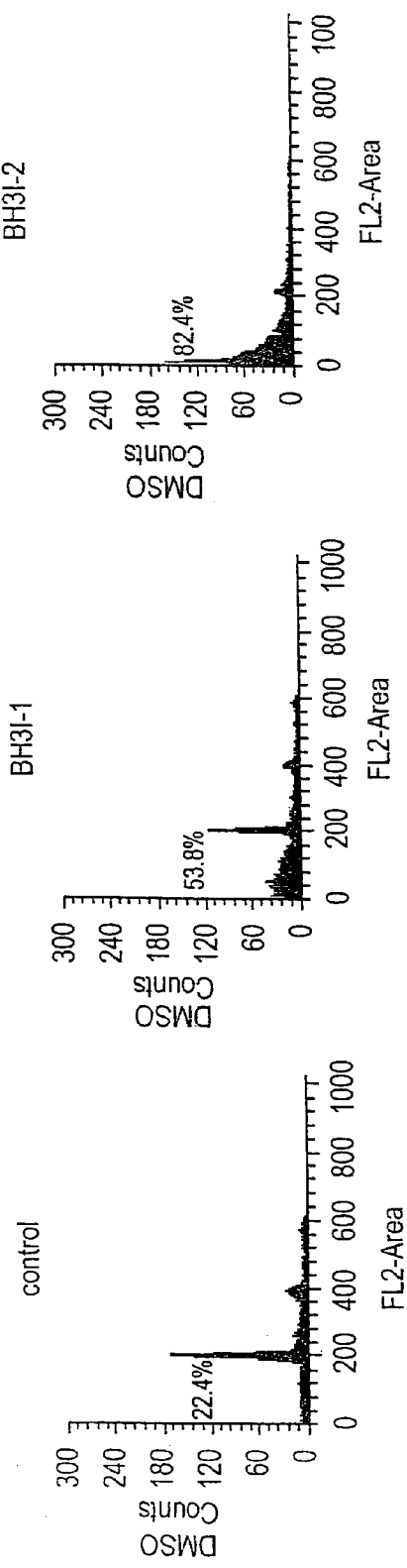
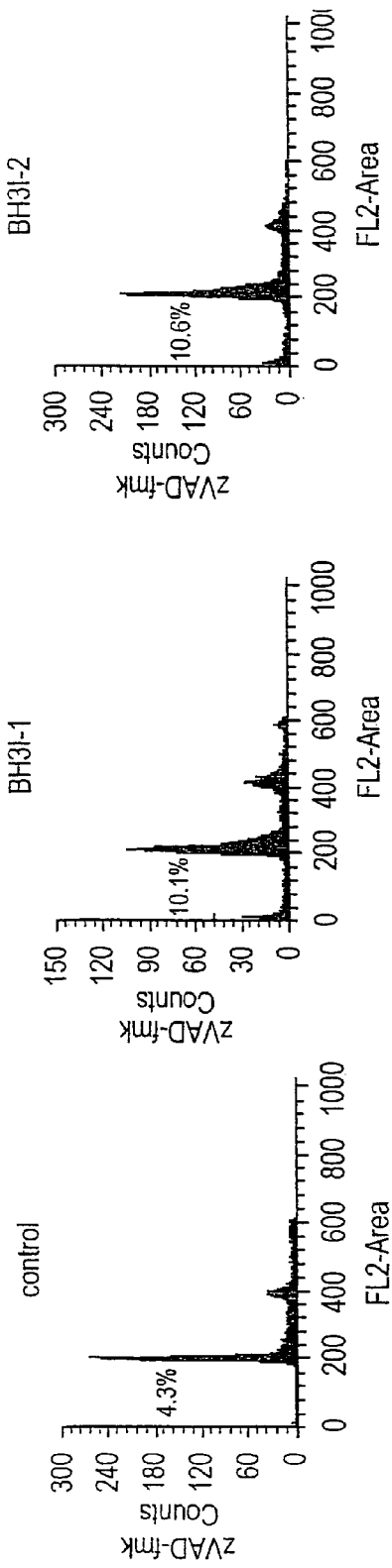
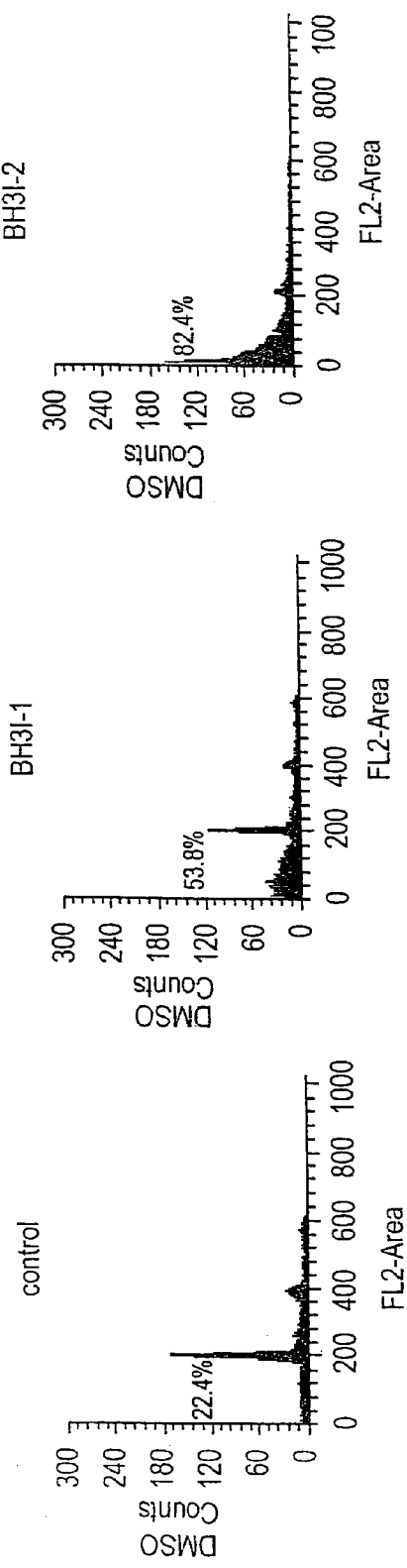
FIG. 10D-1 control
FIG. 10D-2 control
FIG. 10D-3 BH3I-1
FIG. 10D-4 BH3I-1
FIG. 10D-5 BH3I-2
FIG. 10D-6 BH3I-2

SMALL MOLECULES USED TO INCREASE CELL DEATH

CROSS-REFERENCE TO RELATED APPLICATIONS

This application is a divisional of U.S. application Ser. No. 10/802,902, filed Mar. 16, 2004, now U.S. Pat. No. 7,144,905 which is a divisional of U.S. application Ser. No. 10/196,080, filed Jul. 16, 2002, now U.S. Pat. No. 6,706,766 which is a divisional of U.S. application Ser. No. 09/736,502, filed Dec. 13, 2000, now abandoned which claims priority from U.S. Provisional Application No. 60/170,329, filed Dec. 13, 1999, each of which is hereby incorporated by reference.

STATEMENT REGARDING FEDERALLY SPONSORED RESEARCH

This work was supported in part by the Government under Grant No. DAMD 17-98-1-8102 from the Department of the Army. The Government has certain rights in this invention.

BACKGROUND OF THE INVENTION

In general, the invention features methods and compounds for increasing cell death.

Cell growth is a tightly regulated process. When the body has no need for new cells, but cells nonetheless divide in an unregulated manner, the result is cancer. Cancer therapies are directed at controlling the rapid proliferation of cells and/or controlling the differentiation rate of cells, as an undifferentiated cell is highly proliferative. One way in which the proliferation of cancer cells may be controlled is by killing such unregulated dividing cells.

The family of Bcl-2 proteins plays a central role in the regulation of cell life and death, acting by modulating apoptosis, a specific type of cell death. Some members of this family, for example, Bax, Bad, and Bak promote apoptosis, while other members of the family, for example, Bcl-2, Bcl-xL, Bcl-w, and Mcl-1 inhibit apoptosis. The precise mechanism by which the various Bcl-2 family members promote either cell viability or cell death has not yet been resolved.

One method for treating cancer involves controlling the expression and/or activity of Bcl-2 family member proteins. In particular, methods that decrease the expression or activity of anti-apoptotic Bcl-2 family members or increase the expression or activity of pro-apoptotic Bcl-2 family members would be useful for treating cancer.

SUMMARY OF THE INVENTION

The present invention features methods and compounds for disrupting an interaction between a polypeptide containing a Bcl-2-homology-3 domain and another polypeptide, and for increasing cell death. The compounds of the present invention may be used as therapeutics to increase cell death in a desired cell, such as a cancer cell. These compounds are characterized by their ability to inhibit heterodimerization between pro-apoptotic and anti-apoptotic members of the Bcl-2 family of proteins. Identified compounds may be especially useful in treating cancers that overexpress Bcl-2 protein family members.

Accordingly, in a first aspect, the invention features a chemical compound in a pharmaceutically acceptable carrier having the formula:

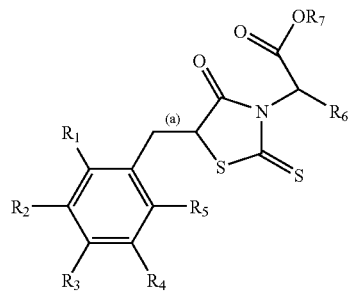

where each of $R_1$, $R_2$, $R_4$, and $R_5$ is independently selected from the group consisting of hydrogen, alkoxyl, hydroxyl, and halogens; $R_3$ is selected from the group consisting of $N(CH_3)_2$, phenyl, hydroxyl, alkoxyl, and halogens; $R_6$ is selected from the group consisting of $CH(CH_3)_2$, $CH_2CH(CH_3)_2$, $CH(CH_3)CH_2CH_3$, and $CH_3$; $R_7$ is either hydrogen or an alkyl group; and the bond (a) is either a single or double bond.

In a preferred embodiment of the above aspect of the invention, the heterocyclic ring of the compound is substituted with a benzyl ring.

In another preferred embodiment, in the compound, each of $R_1$, $R_2$, $R_4$, and $R_5$ are hydrogen; $R_3$ is bromine; $R_6$ is $CH(CH_3)_2$; $R_7$ is hydrogen; and the bond (a) is a double bond.

In yet another preferred embodiment, in the compound, each of $R_1$, $R_2$, $R_4$, and $R_5$ are hydrogen; $R_3$ is chlorine; $R_6$ is $CH(CH_3)_2$; $R_7$ is hydrogen; and the bond (a) is a double bond.

In yet another preferred embodiment, in the compound, each of $R_1$, $R_2$, $R_3$, $R_4$, and $R_5$ are hydrogen; $R_6$ is $CH(CH_3)_2$; $R_7$ is hydrogen; and the bond (a) is a double bond.

In still another preferred embodiment, in the compound, each of $R_1$, $R_2$, $R_4$, and $R_5$ are hydrogen; $R_3$ is $N(CH_3)_2$; $R_6$ is $CH(CH_3)_2$; $R_7$ is hydrogen; and the bond (a) is a double bond.

In other embodiments, the alkoxyl group of $R_1$, $R_2$, $R_4$, $R_5$, or $R_3$ contains 10 or fewer carbons. Preferably the alkoxyl group of $R_1$, $R_2$, $R_4$, $R_5$, or $R_3$ contains 4 or fewer carbons. Most preferably the alkoxyl group of $R_1$, $R_2$, $R_4$, $R_5$, or $R_3$ is a methoxyl group.

In yet other embodiments of the above aspect of the invention, if $R_1$ is hydrogen, then $R_2$, $R_4$, or $R_5$ is not hydrogen; or $R_3$ is not bromine or chlorine; or $R_6$ is not $CH(CH_3)_2$; or $R_7$ is not hydrogen; or the bond (a) is not a double bond. If $R_2$ is hydrogen, then $R_1$, $R_4$, or $R_5$ is not hydrogen; or $R_3$ is not bromine or chlorine; or $R_6$ is not $CH(CH_3)_2$; or $R_7$ is not hydrogen; or the bond (a) is not a double bond. If $R_4$ is hydrogen, then $R_1$, $R_2$, or $R_5$ is not hydrogen; or $R_3$ is not bromine or chlorine; or $R_6$ is not $CH(CH_3)_2$; or $R_7$ is not hydrogen; or the bond (a) is not a double bond. If $R_5$ is hydrogen, then $R_1$, $R_2$, or $R_4$ is not hydrogen; or $R_3$ is not bromine or chlorine; or $R_6$ is not $CH(CH_3)_2$; or $R_7$ is not hydrogen; or the bond (a) is not a double bond. If $R_3$ is bromine or chlorine, then $R_1$, $R_2$, $R_4$, or $R_5$ is not hydrogen; or $R_6$ is not $CH(CH_3)_2$; or $R_7$ is not hydrogen; or the bond (a) is not a double bond. If $R_6$ is $CH(CH_3)_2$, then $R_1$, $R_2$, $R_4$, or $R_5$ is not hydrogen; or $R_3$ is not chlorine or bromine; or $R_7$ is not hydrogen; or the bond (a) is not a double bond. If $R_7$ is hydrogen, then $R_1$, $R_2$, $R_4$, or $R_5$ is not hydrogen; or $R_3$ is not chlorine or bromine; or $R_6$ is not $CH(CH_3)_2$; or the bond (a) is not a double bond. If the bond (a) is a double bond, then $R_1$, $R_2$, $R_4$, or $R_5$ is not hydrogen; or $R_3$ is not chlorine or bromine; or $R_6$ is not $CH(CH_3)_2$; or $R_7$ is not hydrogen.

In a second aspect, the invention features a chemical compound in a pharmaceutically acceptable carrier having the formula:

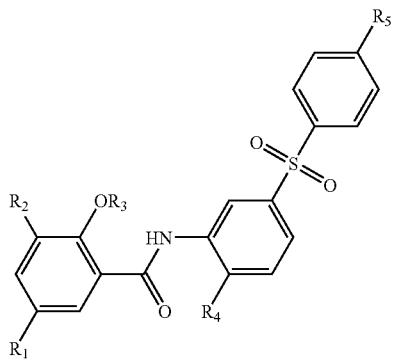

where each of $R_1$, $R_2$, $R_4$, and $R_5$ is, independently, hydrogen, a halogen, or a phenyl group; and $R_3$ is hydrogen or an alkyl group.

In a preferred embodiment of the second aspect of the invention, in the compound, each of $R_1$, $R_4$, and $R_5$ is chlorine; $R_2$ is bromine; and $R_3$ is hydrogen.

In another preferred embodiment of the second aspect of the invention, in the compound, each of $R_1$, $R_4$, and $R_5$ is chlorine; $R_2$ is iodine; and $R_3$ is hydrogen.

In yet another preferred embodiment of the second aspect of the invention, in the compound, $R_1$ and $R_2$ are iodine, $R_4$, and $R_5$ are chlorine; and $R_3$ is hydrogen.

In other embodiments of the second aspect of the invention, if $R_1$ is chlorine, then $R_4$ or $R_5$ is not chlorine; or $R_2$ is not bromine; or $R_3$ is not hydrogen. If $R_4$ is chlorine, then $R_1$ or $R_5$ is not chlorine; or $R_2$ is not bromine; or $R_3$ is not hydrogen. If $R_5$ is chlorine, then $R_1$ or $R_4$ is not chlorine; or $R_2$ is not bromine; or $R_3$ is not hydrogen. If $R_2$ is bromine, then $R_1$, $R_4$, or $R_5$ is not chlorine; or $R_3$ is not hydrogen. If $R_3$ is hydrogen, then $R_1$, $R_4$, or $R_5$ is not chlorine; or $R_2$ is not bromine.

In a third aspect, the invention features a method for increasing cell death, involving the steps of:
(a) providing a cell predicted to be resistant to cell death, or to be at risk for resisting cell death; and
(b) contacting the cell with a chemical compound having the formula:

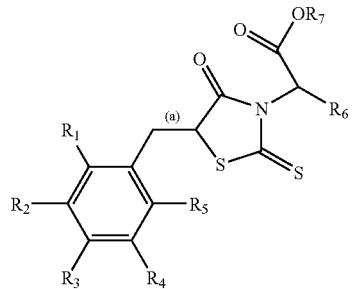

where each of $R_1$, $R_2$, $R_4$, and $R_5$ is independently selected from the group consisting of hydrogen, alkoxyl, hydroxyl, and halogens; $R_3$ is selected from the group consisting of $N(CH_3)_2$, phenyl, hydroxyl, methoxyl, and halogens; $R_6$ is selected from the group consisting of $CH(CH_3)_2$, $CH_2CH(CH_3)_2$, $CH(CH_3)CH_2CH_3$, and $CH_3$; $R_7$ is either hydrogen or an alkyl group; and the bond (a) is either a single or double bond.

In a preferred embodiment of the above aspect of the invention, in the compound, the heterocyclic ring of the compound is substituted with a benzyl ring.

In another preferred embodiment, in the compound, each of $R_1$, $R_2$, $R_4$, and $R_5$ are hydrogen; $R_3$ is bromine; $R_6$ is $CH(CH_3)_2$; $R_7$ is hydrogen; and the bond (a) is a double bond.

In yet another preferred embodiment, in the compound, each of $R_1$, $R_2$, $R_4$, and $R_5$ are hydrogen; $R_3$ is chlorine; $R_6$ is $CH(CH_3)_2$; $R_7$ is hydrogen; and the bond (a) is a double bond.

In yet another preferred embodiment, in the compound, each of $R_1$, $R_2$, $R_3$, $R_4$, and $R_5$ are hydrogen; $R_6$ is $CH(CH_3)_2$; $R_7$ is hydrogen; and the bond (a) is a double bond.

In still another preferred embodiment, in the compound, each of $R_1$, $R_2$, $R_4$, and $R_5$ are hydrogen; $R_3$ is $N(CH_3)_2$; $R_6$ is $CH(CH_3)_2$; $R_7$ is hydrogen; and the bond (a) is a double bond.

In other embodiments, in the compound, the alkoxyl group of $R_1$, $R_2$, $R_4$, $R_5$, or $R_3$ contains 10 or fewer carbons. Preferably the alkoxyl group of $R_1$, $R_2$, $R_4$, $R_5$, or $R_3$ contains 4 or fewer carbons. Most preferably the alkoxyl group of $R_1$, $R_2$, $R_4$, $R_5$, or $R_3$ is a methoxyl group.

In yet other embodiments of the above aspect of the invention, in the compound, if $R_1$ is hydrogen, then $R_2$, $R_4$, or $R_5$ is not hydrogen; or $R_3$ is not bromine or chlorine; or $R_6$ is not $CH(CH_3)_2$; or $R_7$ is not hydrogen; or the bond (a) is not a double bond. If $R_2$ is hydrogen, then $R_1$, $R_4$, or $R_5$ is not hydrogen; or $R_3$ is not bromine or chlorine; or $R_6$ is not $CH(CH_3)_2$; or $R_7$ is not hydrogen; or the bond (a) is not a double bond. If $R_4$ is hydrogen, then $R_1$, $R_2$, or $R_5$ is not hydrogen; or $R_3$ is not bromine or chlorine; or $R_6$ is not $CH(CH_3)_2$; or $R_7$ is not hydrogen; or the bond (a) is not a double bond. If $R_5$ is hydrogen, then $R_1$, $R_2$, or $R_4$ is not hydrogen; or $R_3$ is not bromine or chlorine; or $R_6$ is not $CH(CH_3)_2$; or $R_7$ is not hydrogen; or the bond (a) is not a double bond. If $R_3$ is bromine or chlorine, then $R_1$, $R_2$, $R_4$, or $R_5$ is not hydrogen; or $R_6$ is not $CH(CH_3)_2$; or $R_7$ is not hydrogen; or the bond (a) is not a double bond. If $R_6$ is $CH(CH_3)_2$, then $R_1$, $R_2$, $R_4$, or $R_5$ is not hydrogen; or $R_3$ is not chlorine or bromine; or $R_7$ is not hydrogen; or the bond (a) is not a double bond. If $R_7$ is hydrogen, then $R_1$, $R_2$, $R_4$, or $R_5$ is not hydrogen; or $R_3$ is not chlorine or bromine; or $R_6$ is not $CH(CH_3)_2$; or the bond (a) is not a double bond. If the bond (a) is a double bond, then $R_1$, $R_2$, $R_4$, or $R_5$ is not hydrogen; or $R_3$ is not chlorine or bromine; or $R_6$ is not $CH(CH_3)_2$; or $R_7$ is not hydrogen.

In a fourth aspect, the invention features a method for increasing cell death, said method involving the steps of:
(a) providing a cell predicted to be resistant to cell death, or to be at risk for resisting cell death; and
(b) contacting the cell with a chemical compound having the formula:

In a fifth aspect, the invention features a method for treating a condition in a subject, involving administering a chemical compound having the formula:

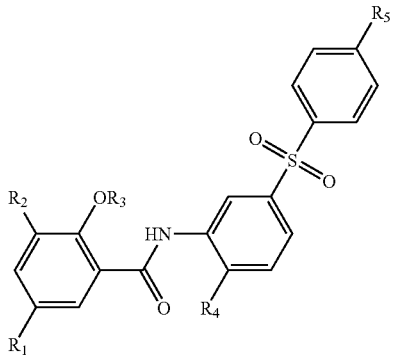

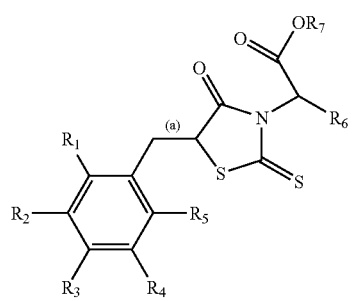

where each of $R_1$, $R_2$, $R_4$, and $R_5$ is, independently, hydrogen, a halogen, or a phenyl group; and $R_3$ is hydrogen or an alkyl group.

In a preferred embodiment of the fourth aspect of the invention, in the compound, each of $R_1$, $R_4$, and $R_5$ is chlorine; $R_2$ is bromine; and $R_3$ is hydrogen.

In another preferred embodiment of the fourth aspect of the invention, in the compound, each of $R_1$, $R_4$, and $R_5$ is chlorine; $R_2$ is iodine; and $R_3$ is hydrogen.

In yet another preferred embodiment of the fourth aspect of the invention, in the compound, $R_1$ and $R_2$ are iodine, $R_4$, and $R_5$ are chlorine; and $R_3$ is hydrogen.

In other embodiments of the fourth aspect of the invention, in the compound, if $R_1$ is chlorine, then $R_4$ or $R_5$ is not chlorine; or $R_2$ is not bromine; or $R_3$ is not hydrogen. If $R_4$ is chlorine, then $R_1$ or $R_5$ is not chlorine; or $R_2$ is not bromine; or $R_3$ is not hydrogen. If $R_5$ is chlorine, then $R_1$ or $R_4$ is not chlorine; or $R_2$ is not bromine; or $R_3$ is not hydrogen. If $R_2$ is bromine, then $R_1$, $R_4$, or $R_5$ is not chlorine; or $R_3$ is not hydrogen. If $R_3$ is hydrogen, then $R_1$, $R_4$, or $R_5$ is not chlorine; or $R_2$ is not bromine.

In one embodiment of the third or fourth aspect of the invention, the cell expresses a pro-apoptotic and/or anti-apoptotic protein. Preferably the pro-apoptotic protein is selected from the group consisting of pro-apoptotic proteins containing a Bcl-2-homology-domain-3, such as Bax, Bak, Bok, Bad, Bid, Bik, Bim, or Hrk. In another embodiment, the anti-apoptotic protein is chosen from the group consisting of Bcl-2, Bcl-xL, Mcl-1, and Bcl-w. In another embodiment, the compound is substantially pure. In another embodiment, the compound is in a pharmaceutically acceptable carrier.

In another embodiment of the third and fourth aspects of the invention, the cell is mammalian. Preferably the cell is a rodent cell, such as a mouse or rat cell. Most preferably, the cell is a human cell. In another embodiment, the cell is a cancer cell.

where each of $R_1$, $R_2$, $R_4$, and $R_5$ is independently selected from the group consisting of hydrogen, alkoxyl, hydroxyl, and halogens; $R_3$ is selected from the group consisting of $N(CH_3)_2$, phenyl, alkoxyl, hydroxyl, and halogens; $R_3$ is selected from the group consisting of $CH(CH_3)_2$, $CH_2CH(CH_3)_2$, $CH(CH_3)CH_2CH_3$, and $CH_3$; $R_7$ is either hydrogen or an alkyl group; and the bond (a) is either a single or double bond.

In a preferred embodiment of the above aspect of the invention, in the compound, the heterocyclic ring of the compound is substituted with a benzyl ring.

In another preferred embodiment, in the compound, each of $R_1$, $R_2$, $R_4$, and $R_5$ are hydrogen; $R_3$ is bromine; $R_6$ is $CH(CH_3)_2$; $R_7$ is hydrogen; and the bond (a) is a double bond.

In yet another preferred embodiment, in the compound, each of $R_1$, $R_2$, $R_4$, and $R_5$ are hydrogen; $R_3$ is chlorine; $R_6$ is $CH(CH_3)_2$; $R_7$ is hydrogen; and the bond (a) is a double bond.

In yet another preferred embodiment, in the compound, each of $R_1$, $R_2$, $R_3$, $R_4$, and $R_5$ are hydrogen; $R_6$ is $CH(CH_3)_2$; $R_7$ is hydrogen; and the bond (a) is a double bond.

In still another preferred embodiment, in the compound, each of $R_1$, $R_2$, $R_4$, and $R_5$ are hydrogen; $R_3$ is $N(CH_3)_2$; $R_6$ is $CH(CH_3)_2$; $R_7$ is hydrogen; and the bond (a) is a double bond.

In other embodiments, in the compound, the alkoxyl group of $R_1$, $R_2$, $R_4$, $R_5$, or $R_3$ contains 10 or fewer carbons. Preferably the alkoxyl group of $R_1$, $R_2$, $R_4$, $R_5$, or $R_3$ contains 4 or fewer carbons. Most preferably the alkoxyl group of $R_1$, $R_2$, $R_4$, $R_5$, or $R_3$ is a methoxyl group.

In yet other embodiments of the above aspect of the invention, in the compound, if $R_1$ is hydrogen, then $R_2$, $R_4$, or $R_5$ is not hydrogen; or $R_3$ is not bromine or chlorine; or $R_6$ is not $CH(CH_3)_2$; or $R_7$ is not hydrogen; or the bond (a) is not a double bond. If $R_2$ is hydrogen, then $R_1$, $R_4$, or $R_5$ is not hydrogen; or $R_3$ is not bromine or chlorine; or $R_6$ is not $CH(CH_3)_2$; or $R_7$ is not hydrogen; or the bond (a) is not a double bond. If $R_4$ is hydrogen, then $R_1$, $R_2$, or $R_5$ is not hydrogen; or $R_3$ is not bromine or chlorine; or $R_6$ is not $CH(CH_3)_2$; or $R_7$ is not hydrogen; or the bond (a) is not a double bond. If $R_5$ is hydrogen, then $R_1$, $R_2$, or $R_4$ is not hydrogen; or $R_3$ is not bromine or chlorine; or $R_6$ is not $CH(CH_3)_2$; or $R_7$ is not hydrogen; or the bond (a) is not a double bond. If $R_3$ is bromine or chlorine, then $R_1$, $R_2$, $R_4$, or $R_5$ is not hydrogen; or $R_6$ is not $CH(CH_3)_2$; or $R_7$ is not hydrogen; or the bond (a) is not a double bond. If $R_6$ is $CH(CH_3)_2$, then $R_1, R_2, R_4$, or $R_5$ is not hydrogen; or $R_3$ is not chlorine or bromine; or $R_7$ is not hydrogen; or the bond (a) is not a double bond. If $R_7$ is hydrogen, then $R_1, R_2, R_4$, or $R_5$ is not hydrogen; or $R_3$ is not chlorine or bromine; or $R_6$ is not $CH(CH_3)_2$; or the bond (a) is not a double bond. If the bond (a) is a double bond, then $R_1, R_2, R_4$, or $R_5$ is not hydrogen; or $R_3$ is not chlorine or bromine; or $R_6$ is not $CH(CH_3)_2$; or $R_7$ is not hydrogen.

In a sixth aspect, the invention features a method for treating a condition in a subject, involving administering a chemical compound having the formula:

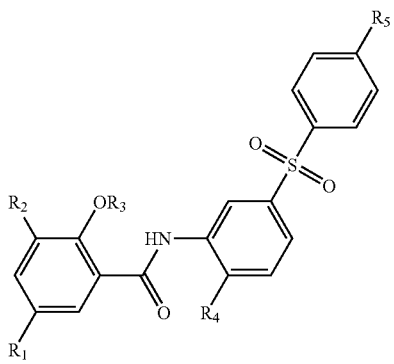

where each of $R_1, R_2, R_4$, and $R_5$ is, independently, hydrogen, a halogen, or a phenyl group; and $R_3$ is hydrogen or an alkyl group.

In a preferred embodiment of the sixth aspect of the invention, in the compound, each of $R_1, R_4$, and $R_5$ is chlorine; $R_2$ is bromine; and $R_3$ is hydrogen.

In another preferred embodiment of the sixth aspect of the invention, in the compound, each of $R_1, R_4$, and $R_5$ is chlorine; $R_2$ is iodine; and $R_3$ is hydrogen.

In yet another preferred embodiment of the sixth aspect of the invention, in the compound, $R_1$ and $R_2$ are iodine, $R_4$, and $R_5$ are chlorine; and $R_3$ is hydrogen.

In other embodiments of the sixth aspect of the invention, in the compound, if $R_1$ is chlorine, then $R_4$ or $R_5$ is not chlorine; or $R_2$ is not bromine; or $R_3$ is not hydrogen. If $R_4$ is chlorine, then $R_1$ or $R_5$ is not chlorine; or $R_2$ is not bromine; or $R_3$ is not hydrogen. If $R_5$ is chlorine, then $R_1$ or $R_4$ is not chlorine; or $R_2$ is not bromine; or $R_3$ is not hydrogen. If $R_2$ is bromine, then $R_1, R_4$, or $R_5$ is not chlorine; or $R_3$ is not hydrogen. If $R_3$ is hydrogen, then $R_1, R_4$, or $R_5$ is not chlorine; or $R_2$ is not bromine.

In another embodiment of the fifth or sixth aspect of the invention, the condition is any condition in which the occurrence of cell death is too low. Preferably the condition is cancer, such as prostate cancer, breast cancer, gastrointestinal cancer, non-small cell lung cancer, colon cancer, melanoma, ovarian cancer, stomach cancer, or a brain tumor, or a leukemia, lymphoma, or carcinoma.

In another embodiment, the subject is a mammal. Preferably the subject is a rodent, such as a mouse or rat. Most preferably the subject is a human.

In another embodiment of the fifth or sixth aspect of the invention, at least two of the compounds are administered, preferably, simultaneously.

In a seventh aspect, the invention features a method for identifying a compound that disrupts an interaction between a first polypeptide containing a Bcl-2-homology-3 domain and a second polypeptide, involving the steps of: providing a test compound, a first polypeptide containing a Bcl-2-homology-3 domain, and a second polypeptide; combining the test compound, first polypeptide, and second polypeptide; and measuring the interaction between the first and second polypeptides, relative to a control that comprises only the first and second polypeptides, where the measuring is done using a fluorescence polarization assay, and where a decrease in the interaction between the first and second polypeptides identifies the test compound as disrupting an interaction between the first and second polypeptides.

In an eighth aspect, the invention features a method for identifying a compound that increases cell death, involving the steps of: contacting a cell with a test compound that disrupts the interaction between a first polypeptide containing a Bcl-2-homology-3 domain and a second polypeptide; and measuring cell death relative to a control cell, where the measuring is done using a fluorescence polarization assay, and where an increase in cell death indicates that the test compound increases cell death.

In one embodiment of the seventh or eighth aspect of the invention, the first polypeptide is chosen from the group consisting of Bax, Bak, Bok, Bad, Bid, Bik, Bim, and Hrk.

By "increasing cell death" is meant increasing the number of cells that undergo cell death relative to a control cell that is not contacted with any test compounds. Preferably cell death is increased 10% relative to a control. More preferably cell death is increased 50% relative to a control. Most preferably cell death is increased is increased 90% relative to a control.

Cell death may be increased by contacting a cell with a test compound. An increase in cell death may be identified by determining the ATP level in a cell that has been contacted with a test compound, such as a small molecule from a chemical library, and comparing it to the ATP level in a control cell, for example, according to the methods of Crouch et al. (J. Immunol. Methods 160:81-8, 1993) Storer et al. (Mutat. Res. 368:59-101, 1996) or Cree et al. (Toxicol. In Vitro 11:553-556, 1997). Cell death is increased when the ATP level of a cell contacted with a test compound decreases more than the ATP level of a control cell. Cell death may also be measured using any of the assays described herein.

By "the occurrence of cell death is too low" or "resistant to cell death" is meant that a cell or a population of cells does not undergo cell death under appropriate conditions. For example, normally a cell will die upon exposure to cytotoxic agents, such as chemotherapeutic agents or ionizing radiation. However, when the occurrence of cell death is too low, for example, in a subject having cancer, the cell or a population of cells may not undergo cell death in response to contact with cytotoxic agents. In addition, the occurrence of cell death may be too low when the number of proliferating cells exceeds the number of cells undergoing cell death, as occurs in cancer when such cells do not properly differentiate.

By "cell death" is meant the death of a cell by either apoptosis or necrosis. Cell death may be characterized by cellular ATP depletion. Preferably the cell is depleted of ATP 10% relative to a control cell. More preferably the cell is depleted of ATP 50% relative to a control cell. Most preferably the cell is depleted of ATP 90% relative to a control cell. The level of cell death may be measured by determining the amount of ATP in a cell.

By "test compound" is meant a chemical, be it naturally-occurring or artificially-derived, that is surveyed for its ability to modulate the level of cell death by employing one of the assay methods described herein. Test compounds may include, for example, peptides, polypeptides, synthesized organic molecules, naturally-occurring organic molecules, nucleic acid molecules, and components thereof. Test compounds also include salts of any of the above chemicals.

By "apoptosis" is meant cell death characterized by any of the following properties: nuclear condensation, DNA fragmentation, membrane blebbing, or cell shrinkage.

By an "anti-apoptotic-protein" is meant a protein which when expressed in a cell decreases cell death, as compared to a cell that does not express the anti-apoptotic protein. Preferably cell death in the cell containing the anti-apoptotic protein is decreased 10% relative to a control. More preferably cell death in the cell containing the anti-apoptotic protein is decreased 50% relative to a control. Most preferably cell death in the cell containing the anti-apoptotic protein is decreased 90% relative to a control.

By a "pro-apoptotic protein" is meant a protein that when expressed in a cell increases cell death, as compared to a cell that does not express the pro-apoptotic protein.

Preferably cell death in the cell containing the pro-apoptotic protein is increased 10% relative to a control. More preferably cell death in the cell containing the pro-apoptotic protein is increased 50% relative to a control. Most preferably cell death in the cell containing the pro-apoptotic protein is increased 90% relative to a control.

By "interacts" is meant a compound that recognizes and binds to an anti-apoptotic protein but which does not substantially recognize and bind to other molecules in a sample.

By "disrupts an interaction" is meant that a test compound decreases the ability of two polypeptides to interact with each other. Preferably the disruption results in a 50% decrease in the ability of the polypeptides to interact with each other. More preferably disruption results in a 75% decrease in the ability of the polypeptides to interact with each other. Most preferably the disruption results in a 99% decrease in the ability of the polypeptides to interact with each other.

As used herein, by "substantially pure" is meant a compound that is at least 60%, by weight, free from proteins and naturally-occurring organic molecules with which it is naturally associated. Preferably the preparation is at least 75%, more preferably 90%, and most preferably at least 99%, by weight, said compound, e.g., a compound from a chemical library. A purified compound may be obtained using methods known to those in the fields of medicinal and organic chemistry.

By "containing a Bcl-2-homology-3 domain" or "containing a BH3 domain" or a "BH3 peptide" is meant a polypeptide that is substantially identical to the amino acid sequence LRRIGDEF (SEQ ID NO: 1).

By "substantially identical" is meant a polypeptide exhibiting at least 60%, preferably 85%, more preferably 90%, and most preferably 95% homology to a reference amino acid sequence.

By "treating" is meant to submit or subject an animal, cell, lysate or extract derived from a cell, or a molecule derived from a cell to a compound that increases cell death.

By "condition" is meant a state of being or feeling. Conditions include, but are not limited to, cancer, for example, prostate cancer, breast cancer, gastrointestinal cancer, non-small cell lung cancer, colon cancer, melanoma, ovarian cancer, stomach cancer, or a brain tumor, or a leukemia, lymphoma, or carcinoma, or the symptoms associated with cancer.

By a "dosage sufficient to increase cell death" is meant an amount of a chemical compound or small molecule which when administered to a subject will increase cell death. Preferably cell death is increased in the subject 10% relative to an untreated subject. More preferably cell death is increased in the subject 50% relative to an untreated subject. Most preferably cell death is increased in the subject 90% relative to an untreated subject.

By a "derivative" is meant a structural derivative having a chemical modification of the compound which does not increase the ultimate level of cell death, but which does enhance bioavailability, solubility, or stability in vivo or ex vivo or which reduces the toxicity or dosage required. Such modifications are known to those skilled in the field of medicinal chemistry.

As used herein, by "measuring cell death" is meant determining if a cell is dying in the presence of a compound compared to a cell that is not in the presence of the compound (control cell). Cell death can be measured by determining cellular ATP levels, wherein a cell that is undergoing cell death has a decreased level of cellular ATP compared to a control cell. Cell death may also be measured by staining with a vital dye, for example, trypan blue, wherein a cell that is dead will be stained with the vital dye, and a cell that is not dead will not be stained with the dye. Cell death can also be measured by contacting a cell with Hoescht stain and viewing it for morphological indications of cell death. Such indications include nuclear fragmentation. Other assays for measuring cell death are described herein.

By "fluorescence polarization assay" is meant an assay in which an interaction between two polypeptides is measured. In this assay, one polypeptide is labeled with a fluorescent tag, and this polypeptide emits nonpolarized light when excited with polarized light. Upon an interaction of the tagged polypeptide with another polypeptide, the polarization of emitted light is increased, and this increased polarization of light can be detected.

The present invention provides a number of advantages. For example, the methods described herein allow for an increase in cell death or a disruption of the interaction between Bcl-2 family members. The invention also provides compounds and methods for treating diseases in which a cell is resistant to cell death. These compounds and methods can be used to treat conditions such as cancer.

Other features and advantages of the invention will be apparent from the following detailed description and from the claims.

BRIEF DESCRIPTION OF THE DRAWINGS

FIG. 10D-1-10D-6 are a series of graphs showing DNA fragmentation analysis of Jurkat cells treated with BH3Is and zVAD-fmk. Cells were treated with DMSO (blank; 1 and 2), BH3I-1 (100 µM; 3 and 4), or BH3I-2 (30 µM; 5 and 6) in the presence (1, 3, and 5) or absence (2, 4, and 6) of zVAD-fmk for 72 hr. The cells were then fixed and stained with propidium iodide (PI). Samples were analyzed by FACS, and the percentage of subG1 DNA is shown for each sample.

DETAILED DESCRIPTION OF THE INVENTION

Figure 1:
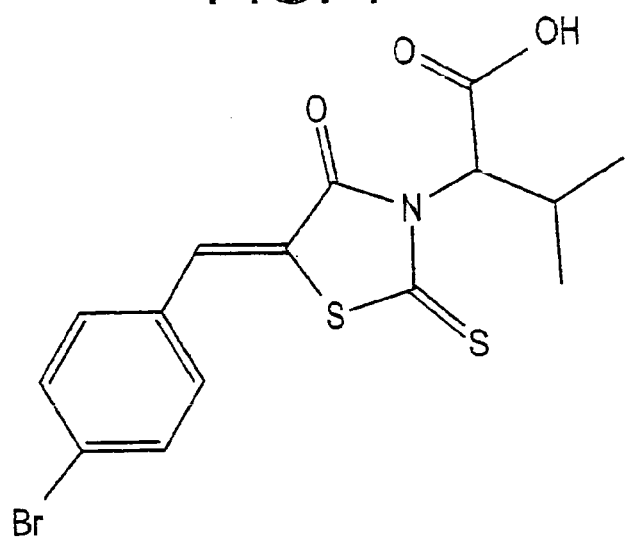
FIG. 1 is a schematic representation of the chemical structure of chemical compound ID number 275805 (BH3I-1) from the CheiBridge chemical compound library.

Described herein are methods for increasing cell death, as well as for treating a condition in a subject. Techniques for carrying out the methods of the invention are now described in detail.

Identification of Chemical Compounds that Inhibit Heterodimerization of Bcl-2 Protein Family Members It has been well established that members of the Bcl-2 family are involved in the regulation of cell viability and cell death. The precise mechanism through which this regulation occurs has not been fully elucidated. However, it is known that various Bcl-2 family members can dimerize with each other. Bcl-2 family members that promote cell viability can form homodimers or heterodimers with other viability-promoting family members, or can form heterodimers with apoptosis-promoting family members. It has been proposed that the ability of a cell to undergo apoptosis depends on the level of pro-apoptotic proteins within a cell which are not heterodimerized to a viability promoting protein such as Bcl-2 or Bcl-xL (Taylor et al., Nat. Biotech. 17:1097-1100, 1999; Kang et al., Neurosci. Lett. 256:8928-35, 1998; Shibata et al., EMBO J. 18:2692-2701, 1999; Thomas et al. Oncogene 12:1055-1062, 1996; Miyashita et al., Oncogene 9:1799-1805, 1994; and Motoyama et al., Science 267:1506-1510, 1995). The greater the amount of undimerized pro-apoptotic protein in a cell, the greater the likelihood is that the cell will die.

To tip the scales of this pathway in favor of cell death, one may increase the amount of free pro-apoptotic protein in a cell. This may be done by preventing the heterodimerization of an apoptosis-promoting protein and an anti-apoptosis-promoting protein, for example, by administering a small molecule inhibitor of such an interaction to a cell. Furthermore, it has been suggested through NMR studies, that heterodimerization between anti-apoptotic proteins and pro-apoptotic proteins is mediated through the Bcl-2-homology-3 domain, or BH3 domain, of the pro-apoptotic Bcl-2 family members and the Bcl-2-homology-1, 2, and 3 domains (BH1, BH2, and BH3 domains) of the anti-apoptotic Bcl-2 family members. For example, the pro-apoptotic protein Bak interacts with the anti-apoptotic protein Bcl-xL through its BH3 domain (Sattler et al. Science 275:983-986, 1997). Therefore, a small molecule that inhibits the interaction of anti-apoptotic proteins and pro-apoptotic proteins would be useful for promoting cell death.

We have used a fluorescence polarization assay to screen a library of 16,000 chemical compounds (ChemBridge, San Diego, Calif.) to identify small molecules that inhibit the interaction between a peptide corresponding to the BH3 domain of a pro-apoptotic protein and a recombinant Bcl-xL/GST fusion protein. In this assay, an eighteen amino acid peptide corresponding to the BH3 domain of Bak was used. The Bak peptide was labeled with a fluorescent tag, such as OREGON GREEN. Upon binding of the tagged peptide to the Bcl-xL/GST fusion protein, the polarization of light emitted by the tagged peptide is altered. Therefore, in a sample in which a compound from the chemical library does not inhibit the interaction between the Bak peptide and the Bcl-xL/GST fusion protein the polarization of light emitted by the peptide will be altered. Conversely, in a sample in which a compound does inhibit the interaction between the Bak peptide and the Bcl-xL/GST fusion protein the polarization of light emitted by the peptide will not be altered.

The interaction between two polypeptides may be assessed by other means known to those skilled in the field of molecular biology. For example, the interacting proteins may be co-immunoprecipitated using an antibody that recognizes either of the polypeptides, using methods commonly known in the art.

Similar assays can be performed using other members of the Bcl-2 family. For example, other pro-apoptotic Bcl-2 family members that contain a BH3 domain may be substituted for the Bak polypeptide in the above-described assay. Alternatively, peptides from other anti-apoptotic Bcl-2 family members may be substituted for Bcl-xL in the fusion protein in the above assay. Carrying out this assay using various Bcl-2 family members will identify compounds that can be used to increase cell death.

Identification of Compounds that Inhibit Heterodimerization of Bcl-2 Family Proteins and Increase Cell Death Compounds from the chemical library identified to inhibit the interaction between a Bak peptide and a Bcl-xL/GST fusion protein, or other pro-apoptotic/anti-apoptotic Bcl-2 family member interactions, as described above, may also increase cell death. To determine this, a cell may be administered a compound and the level of cell death that occurs may be measured and compared to the level of cell death that occurs in a cell which was not administered the compound. The level of cell death may be measured, for example, by determining cellular ATP levels according to the methods of Crouch et al. (supra), Storer et al. (supra), or Cree et al. (supra), wherein a decrease in the cellular ATP level indicates an increase in cell death. Alternatively, cell death may be measured by staining a cell with a vital dye, such as trypan blue, wherein the staining of a cell with a vital dye indicates that the cell is dead. Accordingly, if a population of cells receiving a candidate compound exhibits increased cell death, relative to an untreated control population of cells, then the candidate compound increases cell death.

Various types of cells may be used to carry out the invention. For example, immortalized cells, such as HeLa cells, U-937 cells, and Jurkat cells may be used. Alternatively, cells may be transfected with a transgene that promotes resistance to cell death, and used in the invention. For example, HeLa cells may be stably transfected with a viability-promoting member of the Bcl-2 family, for example Bcl-xL.

Structural Derivatives of Chemical Compounds that Increase Cell Death

The small molecules identified to increase cell death may be structurally modified and subsequently used to increase cell death, or to treat a subject with a condition in which the occurrence of cell death is too low. For example, the small molecules may be modified by any of the following processes: substitution of a valine moiety with leucine, isoleucine, or alanine; substitution of a heterocyclic ring with a benzyl ring; reduction of a double bond attached to a heterocyclic ring; introduction of additional constituents, for example, hydroxyl, alkoxyl, or halogen groups at various positions of a benzyl ring; substitution of bromine or chlorine moieties with a hydroxyl, alkoxyl, or phenyl group or derivative of a phenyl group; conversion of a carboxyl group into an ester; elimination of various halogen groups; etherification of a hydroxyl group; or substitution of a halide group with a phenyl group, or a derivative of a phenyl group.

Therapy

A compound identified as capable of increasing cell death by any of the above-described methods may be administered within a pharmaceutically-acceptable diluent, carrier, or excipient, in unit dosage form. Conventional pharmaceutical practice may be employed to provide suitable formulations or compositions to administer the identified compound to patients suffering from a disease in which there is a lack of cell death. Administration may begin before the patient is symptomatic. Any appropriate route of administration may be employed, for example, administration may be parenteral, intravenous, intraarterial, subcutaneous, intramuscular, intracranial, intraorbital, ophthalmic, intraventricular, intracapsular, intraspinal, intracisternal, intraperitoneal, intranasal, aerosol, by suppositories, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (19th ed., ed. A. R. Gennaro AR., 1995, Mack Publishing Company, Easton, Pa.). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds that increase cell death include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with a compound identified according to the methods described above, may be combined with more traditional therapies for the disease characterized by a lack of cell death, for example, traditional chemotherapeutic agents, radiation therapy, or surgery.

The methods of the instant invention may be used to increase cell death as described herein in any mammal, for example, humans, domestic pets, or livestock.

The following examples are provided to illustrate the invention. These examples should not be construed as limiting.

EXAMPLE 1

Identification of Small Molecules that Inhibit Interaction Between a Bak Polypeptide and a Bcl-xL/GST Fusion Protein A nineteen amino acid Bak peptide, corresponding to the BH3 domain of Bak, with the sequence KGGGQVGRQLAI-IGDDINR (SEQ ID NO: 2) was labeled with the fluorophore OREGON GREEN according to the manufacturer's instructions (Molecular Probes, Eugene, Oreg.). In addition, a recombinant Bcl-xL/GST fusion protein was generated using conventional techniques known to those skilled in the fields of biochemistry and molecular biology. The interaction between the Bak peptide and the Bcl-xL/GST fusion protein was confirmed.

A screen of approximately 16,000 compounds from the ChemBridge chemical compound library was conducted to identify compounds that disrupt the interaction between the Bak peptide and the Bcl-xL/GST fusion protein. The ability of a compound to disrupt the interaction between the two polypeptides was assessed using a fluorescence polarization assay. The Bak peptide and Bcl-xL/GST fusion protein (15 nM each; dissolved in PBS) were first combined, and then the compound was added. Alternatively, the Bak peptide, Bcl-xL/GST fusion protein, and test compound (5 mg/ml; dissolved in 0.1-0.5 gl of DMSO) may be combined in any order. Normally the unbound Bak polypeptide results in polarization of approximately 40 mP units. Upon binding of the Bcl-xL/GST fusion protein, polarization increased to approximately 100-120 mP units.

In a preferred method, the fluorescence assay was carried out as follows. Bak BH3 peptide (Research Genetics) was labeled using NHS-OREGON GREEN (Molecular Probes) and purified by HPLC. For the initial screening assays, 33 nM of labeled BH3 peptide, 2 µM of GST-Bcl-xL protein, 0.1% bovine gamma globulin (BGG, Sigma) and 1 mM DTT mixed with PBS, pH 7.2 (Gibco) were added into 384 well black plates (Lab Systems) using MULTIDROP (Lab Systems). Small molecules (5 mg/ml in DMSO, ChemBridge) were transferred using plastic 384-pin arrays (Genetix). The plates were incubated for 1-2 hr at 25° C., and the fluorescence polarization assay values were determined using an Analyst plate reader (LJL Biosystems). Reactions containing 16.65 nM of labeled BH3 peptide and 4.2 µM of Bcl-xL-His$_6$ fusion protein, which was previously utilized to characterize BH3/Bcl-xL binding (Sattler et al., Science 275:983-6, 1997) were used for the further fluorescence polarization analyses. Kd and Ki determination was performed as previously described using GRAPHPAD PRISM software package (GraphPad) (Dandliker et al., Methods Enzymol. 74:3-28,1981).

In a primary screen of the approximately 16,000 chemical compounds from the ChemBridge library, approximately 10 compounds were identified to disrupt the interaction between Bak and the Bcl-xL/GST fusion protein. Each of these compounds had a Ki value of 50 µM or lower. These compounds were selected for a secondary screen. Chemicals for further testing were obtained from ChemBridge, except for BH3I-1''', which was obtained from Chemical Diversity.

Figure 2:
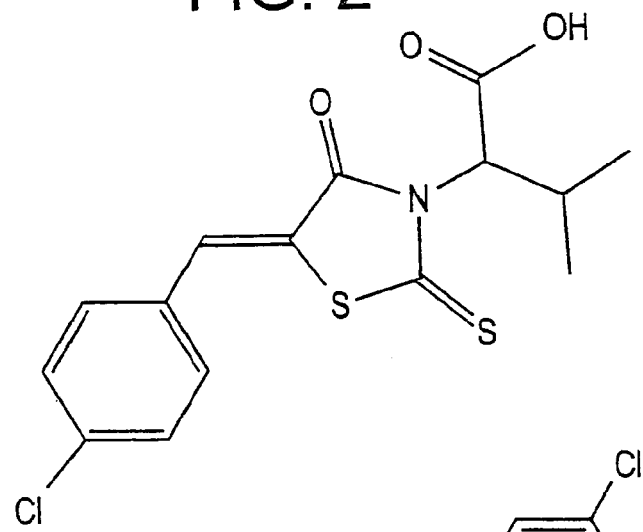
FIG. 2 is a schematic representation of the chemical structure of chemical compound ID number 282986 (BH3-I-1') from the Chemnridge chemical compound library.
Figure 3:
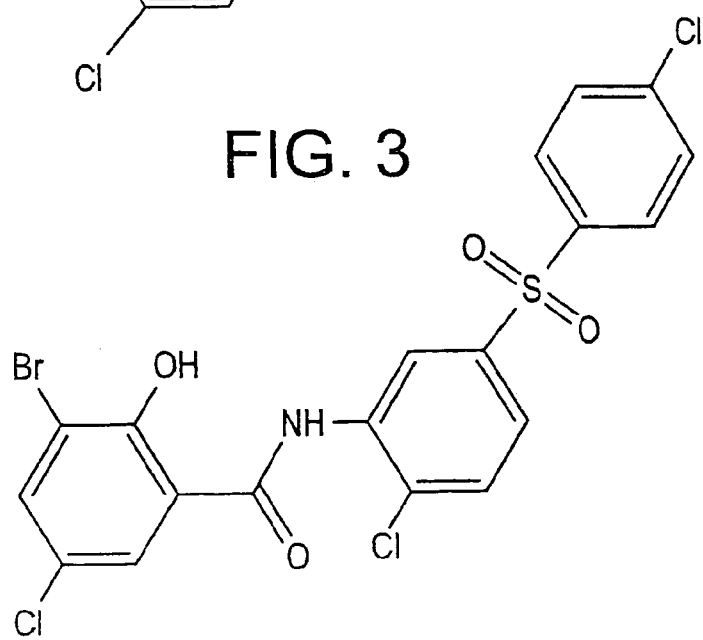
FIG. 3 is a schematic representation of the chemical structure of chemical compound ID number 175362 (BH3I-2) from the ChemBridge chemical compound library.
Figure 4:
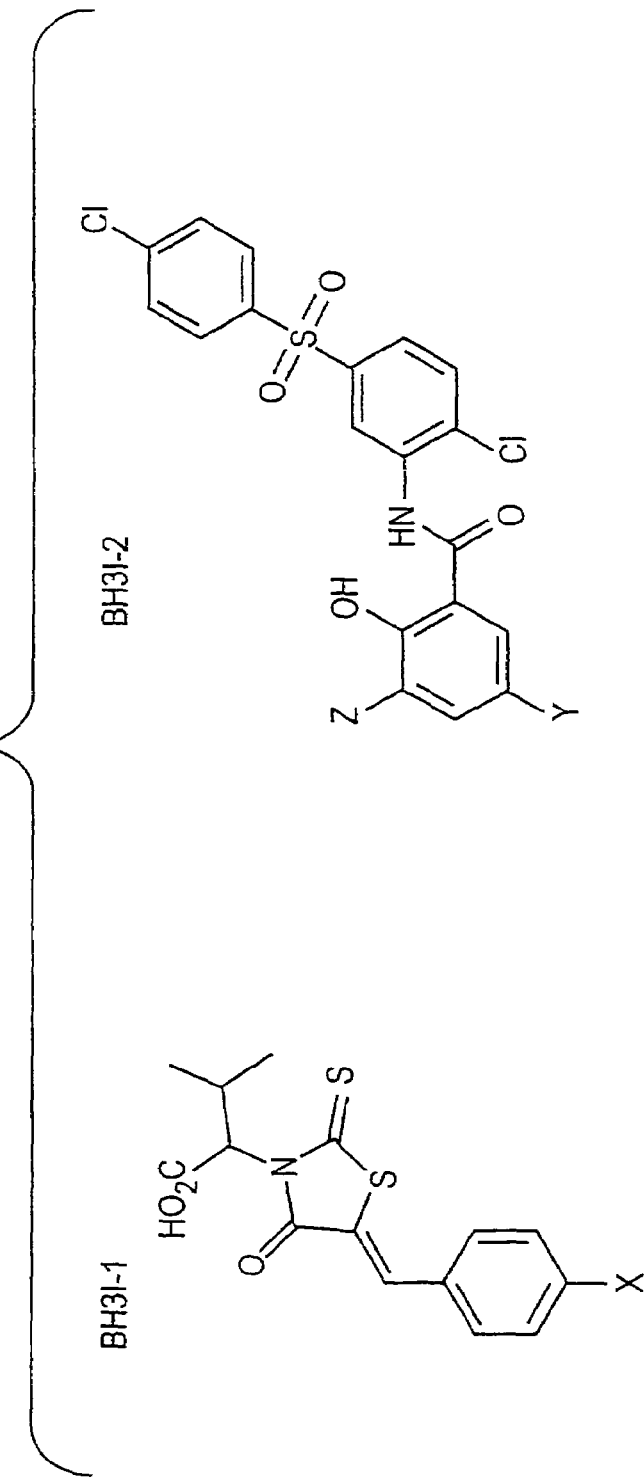
FIG. 4 shows two schematic representations of the structures and chemical names of the compounds selected in the screen. The Ki values for the inhibition of Bak/Bcl-xL-His$_6$ interaction, determined using fluorescence polarization and NMR titration assays, are shown with the standard deviation values.

In a further screen, various concentrations of each of the above-identified compounds were evaluated for their potency. A serial dilution of each chemical compound was performed and the fluorescence polarization assay was repeated, as per the primary screen. As a result of the secondary screening, three compounds, chemical compound ID numbers 275805 (BH3I-1; FIG. 1), 282986 (BH3I-1'; FIG. 2), and 175362 (BH3I-2; FIG. 3), collectively termed "BH3Is," were identified to disrupt the interaction between Bak and the BCL-$x_L$/GST fusion protein. Each of these compounds displayed a Ki value of 10-20 µM in the fluorescence polarization assay. Additional homologues of the BH3I-1s (BH3I-1" and BH3I-1''') and BH3I-2 (BH3-2" and BH3I-2") were also analyzed in the study (FIG. 4). According to the results of the fluorescence polarization assays, the affinity of the inhibitors was in the low µM range, with affinities decreasing in the following order: BH3I-1>BH3I-1'>BH3I-2'>BH3I-2>BH3I-2">BH3I-1". The affinity of BH3I-1''' using the fluorescence polarization assay was not assessed, because of its intrinsic fluorescence.

EXAMPLE 2

BH3Is Inhibit Bcl-xL Heterodimerization in Vitro

To test the possibility that BH3Is target the OREGON GREEN moiety of the fluorescently labeled BH3 peptide, a novel BH3/Bcl-xL binding assay using unlabeled BH3 peptide was designed. In this assay Bcl-xL was covalently attached to a surface-enhanced laser desorption/ionization (SELDI) chip, and binding of the unlabelled BH3 peptide to the immobilized protein was monitored by mass spectrometry. Specifically, purified recombinant GST-Bcl-2 and BCL-xL-$His_6$ were coupled through their primary amines to SELDI chip surfaces derivatized with carbonyldiimidazole (Ciphergen). Bak BH3 peptide was then added (in a total volume of 1 µl) for 12 hours at 4° C. in a humidified chamber, to allow binding to each spot of the SELDI chip. The chip was then washed with alternating high and low pH-0.1M sodium acetate with 0.5M NaCl, followed by 0.01M HEPES; pH 7.3. The samples were embedded in α-cyanno-4-hydroxycinnamaic acid matrix and analyzed for mass by MALDI TOF. An average of 100 laser shots at a constant setting were collected over 20 spots in each sample.

Figure 5A:
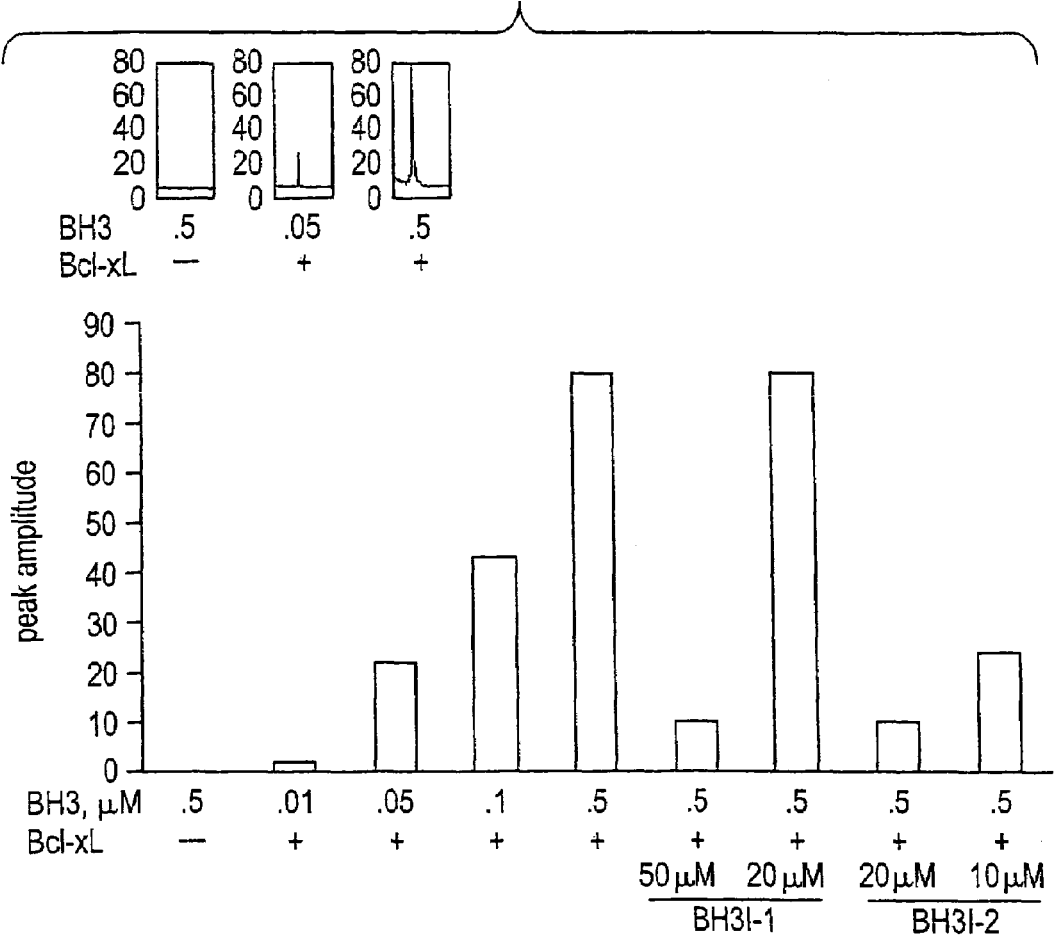
FIG. 5A is a graph showing the binding of increasing amounts of the Bak BH3 peptide to SELDI surfaces modified with 2 pmoles of Bcl-xL-His$_6$ in the presence or absence of the indicated amounts of BH3Is. The insert of this figure shows examples of actual mass spectrometry data.
Figure 5B:
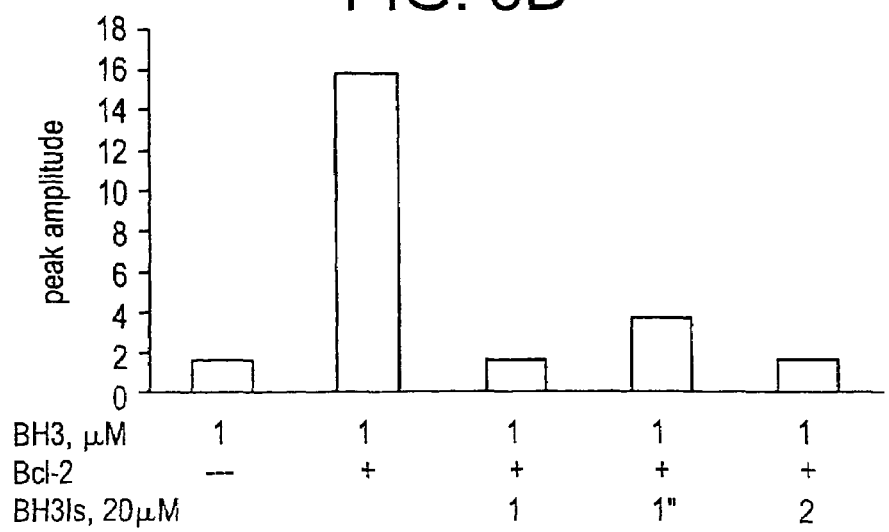
FIG. 5B is a graph showing the effects of BH3Is on the binding of Bak BH3 peptide to Bcl-2. Bak BH3 peptide was incubated with SELDI surfaces modified with 5 pmoles of GST-Bcl-2 in the presence or absence of the indicated concentrations of BH3Is. As a negative control ( - - - ), Bak BH3 peptide was incubated with SELDI surface without Bcl-xL/Bcl-2 proteins.

BH3 peptide bound to the Bcl-xL-modified surface in a dose-dependent fashion (FIG. 5A). Addition of BH3I-1 or BH3I-2 resulted in the reduction of BH3 binding. BH3I-2 had higher activity than BH3I-1 in this assay. Similar to the fluorescence polarization assay results, BH3I-1" showed lower potency than BH3I-1 in this assay. In addition, BH3Is disrupted the BH3/Bcl-2 interaction (FIG. 5B). In this study, Bak BH3 peptide was incubated with SELDI surface modified with 5 pmoles of GST-Bcl-2 in the presence or absence of BH3Is. As a negative control Bak BH3 peptide was incubated with SELDI surface without Bcl-xL/Bcl-2 proteins. These data suggest that BH3Is can target multiple anti-apoptotic Bcl-2 family members.

Next, it was determined whether BH3Is could disrupt the heterodimerization of Bcl-xL with pro-apoptotic proteins from the Bcl-2 family, such as truncated Bid (tBid). Truncation of Bid by caspase-8 activates Bid and dramatically increases its affinity towards anti-apoptotic Bcl-2 family members (Li et al., Cell 94:491-501, 1998). To perform this study, in vitro translation of tBid or $U2AF^{65}$ (control) was performed using TNT® Coupled Reticulocyte and Wheat Germ Lysate Systems (Promega) respectively. Bcl-xL, $U2AF^{35}$ (control) or corresponding amounts of original Ni-NTA agarose beads (blank) were pre-incubated with the BH3I inhibitors or peptide in 100 µl of PBS for 30 min at 25° C. Then 1 µl of $^{35}$S-labeled tBID or $U2AF^{65}$ was added and incubation was continued for 2 hr at 4° C. The samples were subjected to SDS-PAGE, coomassie blue staining and autoradiography.

Figure 5C:
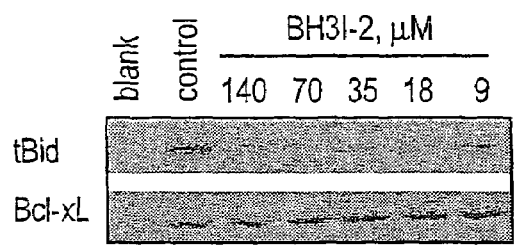
FIG. 5C is an image of an autoradiograph of tBid expression and coomassie blue images of Bcl-xL from pulldown experiments. Bcl-xL-His$_6$-containing agarose beads were pre-incubated with the indicated concentrations of BH3I-2, and then with $^{35}$S labeled in vitro translated tbid. Ni-NTA (Qiagen) beads without protein were used as a negative control (blank).
Figure 5D:
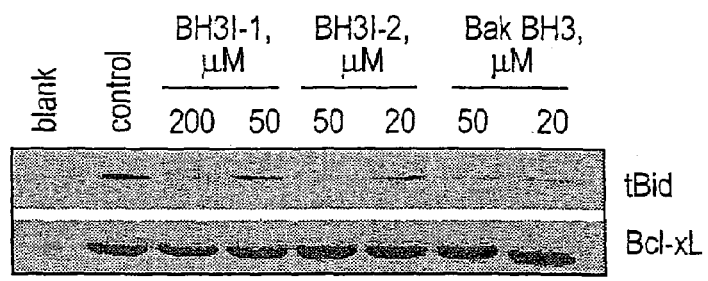
FIG. 5D is an image of an autoradiograph of tBid expression and coomassie blue images of Bcl-xL from pulldown experiments. Bcl-xL-His$_6$-containing agarose beads were pre-incubated with the indicated concentrations of BH3I-2, BH3I-1, and Bak BH3 peptide, and then with $^{35}$S labeled in vitro translated tBid. Ni-NTA (Qiagen) beads without protein were used as a negative control (blank).

In vitro translated tBid specifically bound to His-tagged Bcl-xL immobilized on $Ni^{2+}$ beads (FIG. 5C). Addition of either BH3I-2 or BH3I-1 resulted in a dose-dependent decrease in the tBid binding. BH3I-1 showed lower activity than BH3I-2 (FIG. 5D), and the activity of BH3I-1" was even lower.

The results of the tBid pulldown and SELDI assays indicate that the use of OREGON GREEN moiety in fluorescence polarization assays could have resulted in an overestimation of the Ki values of the BH3I-1s relative to BH3I-2s. To verify this conclusion, NMR titrations of Bcl-xL with BH3I-1s were performed and their Ki values were determined (FIG. 4). The results of NMR titrations showed that the relative order of affinities of BH3I-1s is: BH3I-1>BH3I-1'>BH3I-1">BH3I-1'''. Moreover, the NMR derived Ki value of BH3I-1 was lower than the fluorescence polarization assay derived Ki value of BH3I-2. The Ki value for BH3I-2 was not able to be verified using NMR titrations because of the predominantly intermediate exchange rate displayed by this compound. The BH3I-1s Ki values obtained by the NMR approach agree with the results of both pulldown and SELDI analyses. Therefore, the order of affinities of BH3Is is: BH312'>BH3I-2>BH3I-2">BH3I-1>BH3I-1'>BH3I-1">BH3I-1'''.

EXAMPLE 3

BH3Is Are Selective Inhibitors of Bcl-2 Family Proteins

Figure 5E:
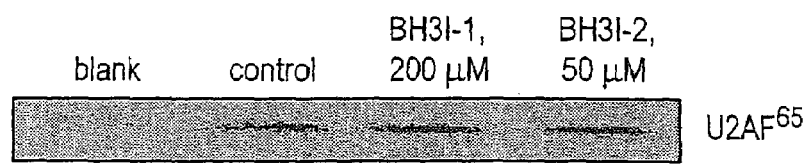
FIG. 5E is an image of an autoradiograph of U2AF$^{65}$ expression from pulldown experiments. U2AF$^{35}$-His$_6$-containing agarose beads were pre-incubated with the indicated concentrations of BH3I-2, BH3I-1, and then with $^{35}$S labeled in vitro translated U2AF$^{65}$. Ni-NTA (Qiagen) beads without protein were used as a negative control (blank).

To determine the specificity of BH3Is, their ability to inhibit other protein-protein interactions was tested using the pulldown assay described above and the splicing factors $U2AF^{35}$ and $U2AF^{65}$ (Zhang et al, Proc. Natl. Acad. Sci. USA 89:8769-73, 1992). Neither BH3I-1 nor BH3I-2 affected the interaction between the splicing factors (FIG. 5E). BH3Is (80 µM) also had no effect on the interaction between the Apaf-1 CARD domain fragment and caspase-9 in the SELDI assay.

Since NMR spectroscopy allows the detection of low-affinity (up to Kd=1 mM) interactions, it was used to confirm the absence of inhibition of the control protein-protein interactions by BH3Is. BH3Is did not affect the interactions between the CIDE-N domains of CIDE-B and DFF40 or DFF45 (Lugovskoy et al., Cell 99:747-55, 1999). Despite close structural homology between full length Bid and Bcl-xL, the BH3Is failed to bind Bid. Therefore, these compounds demonstrate a high degree of specificity (Chou et al., Cell 96:615-24, 1999; and McDonnell et al., Cell 96:625-34, 1999).

EXAMPLE 4

Small Molecules That Inhibit Interaction Between a Bak Polypeptide and a Bcl-$x_L$/GST Fusion Protein Also Increase Cell Death The BH3I compounds that were found to disrupt the interaction between a Bak peptide and a BCL-xL/GST fusion protein were evaluated for their cytotoxic effects. HeLa cells, U-937 cells, or Jurkat cells, each of which endogenously express both Bak and Bcl-xL, were contacted with each of the BH3I chemical compounds identified above, by adding the compound to the cell culture media. Forty-eight hours after the cells received the chemical compound the cell culture sample was evaluated for the level of cell death that had occurred in response to the chemical compound. The level of cell death was determined by measuring cellular ATP levels, wherein a decrease in cellular ATP levels indicated an increase in cell death. In each cell line, cell death was increased in the sample that received one of the above-identified compounds. In each cell line, chemical compounds 275805 (BH3I-1) and 282986(BH3I-1') displayed GI50 values of 50-70 µM, while chemical compound 175362 (BH3I-2) displayed a GI50 value of 10-15 µM. In addition, the cells treated with the above chemical compounds and subsequently stained with Hoescht exhibited extensive nuclear fragmentation, indicating that apoptosis was occurring in the cells.

Figure 6A:
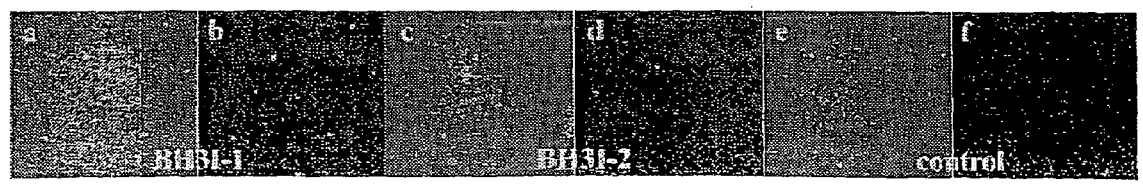
FIG. 6A is a series of images showing the viability of cells treated with various BH3Is.
Figure 6B:
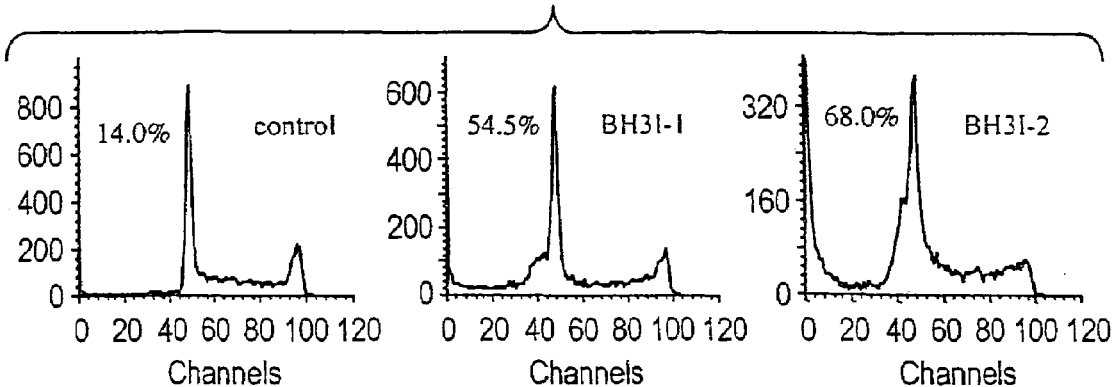
FIG. 6B is a set of graphs showing the percentage of subG 1 cells in a population of cells left untreated (left), treated with BH3I-1 (center), or treated with BH3I-2 (right).
Figure 6C:
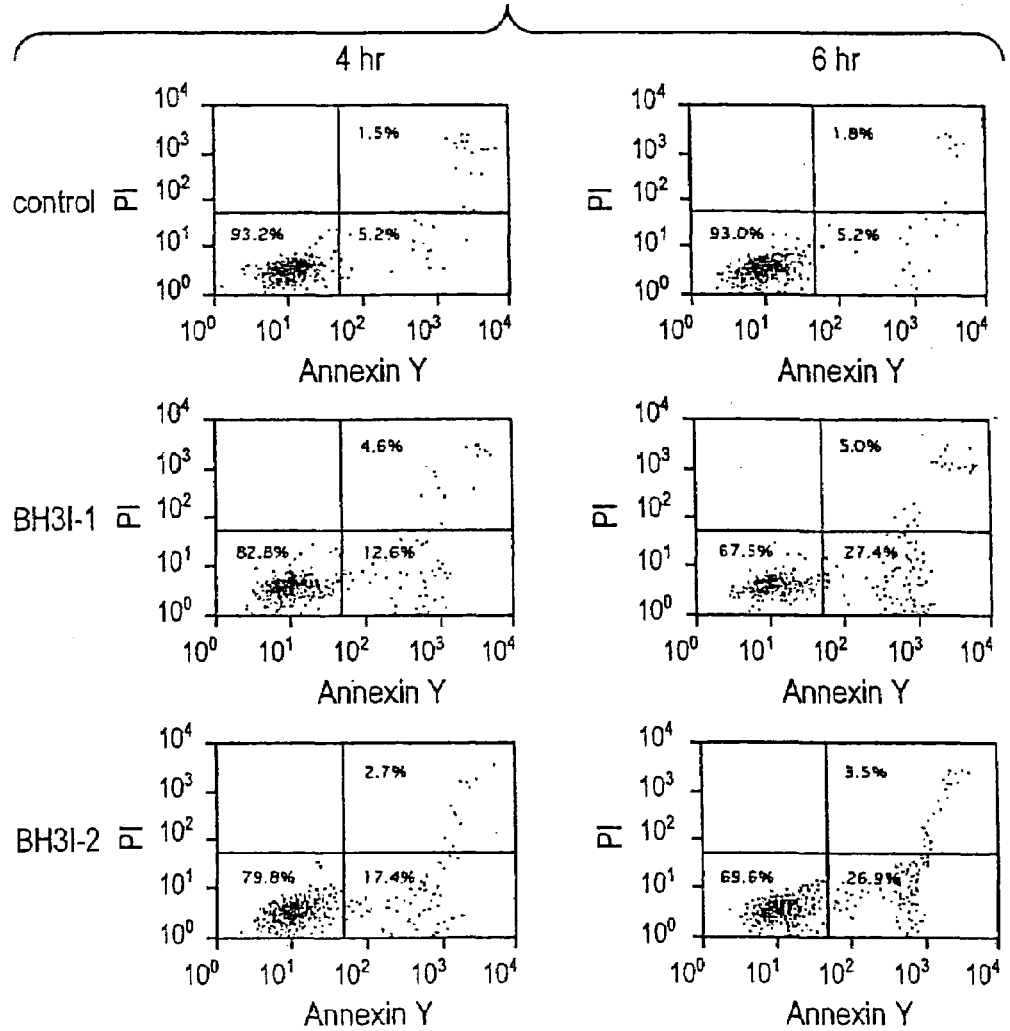
FIG. 6C is a series of FACS analysis graphs showing Annexin V staining of Jurkat cells. Jurkat cells were treated with BH3I-1 (100 μM) or BH3I-2 (30 μM) and were stained 4 or 6 hr later with Annexin V-EGFP/PI. The relative amounts of live, apoptotic, and late apoptotic/necrotic cells are shown.

To further examine the ability of BH3Is to induce apoptosis, Jurkat cells were treated with BH3I-1 (100 µM) (FIG. 6A, panels a and b), BH3I-2 (30 µM) (FIG. 6A, panels c and d) or DMSO (FIG. 6A, panels e and f) for 48 hr. The cells were then stained using Hoechst dye and a FragEL TUNEL kit (Oncogene Research Products). The treatment resulted in TUNEL positivity, indicating that the BH3Is induced DNA fragmentation. In addition, a significant portion of the cells treated with a BH3I displayed sub-G1 DNA content, which is indicative of apoptosis (FIG. 6B). This was determined by treating Jurkat cells with BH3I-1 (100 µM) or BH3I-2 (30 µM), fixing them 72 hr later, and staining them with propidium iodide (PI). The samples were analyzed by FACS. Finally, BH3Is induced the appearance of Annexin V binding without an increase in PI staining (FIG. 6C). These results demonstrate that treatment of cells with a BH3I induces apoptosis.

Figure 6D:
FIG. 6D is a set of images of cells showing cytochrome c release induced by BH3Is. HeLa cells were treated with 100 μM BH3I-1 for 48 hr and were then stained with Hoechst (a) or cytochrome c antibody (b). The arrows indicate the position of an apoptotic cell.
Figure 6E:
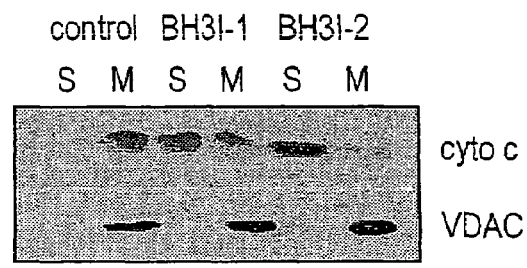
FIG. 6E is an image of a Western blot analysis of cytochrome c release from Jurkat cells treated with BH3I-1 (100 μM) or BH3I-2 (50 μM) for 48 hr. Cells were fractionated and soluble (S) and heavy membrane (M) fractions were subjected to Western blot analysis using cytochrome c (Pharmingen) and VDAC (Calbiochem) antibodies.

Next, the role of BH3 Is in inducing the release of cytochrome c from mitochondria was examined. Immunostaining with cytochrome c antibody and fractionation experiments showed that BH3I-1 (FIGS. 6D and 6E) and BH3I-2 (FIG. 6E) induced cytochrome c release. $DiOC_6$ staining failed to demonstrate a decrease in mitochondrial membrane potential in cells treated with BH3Is for 48 hr.

Figure 6F:
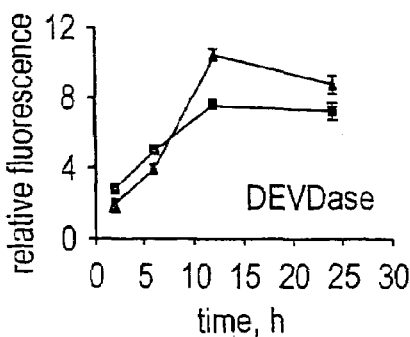
FIG. 6F is a graph showing the time course of caspase activation in Jurkat cells, as assayed using a QuantiPak kit (Biomol). The cells were treated with 100 μM of BH3I-1 (triangles) or 50 μM of BH3I-2 (squares) for 2, 6, 12, or 24 hr. A fluorescence based assay of caspase-3 (Ac-DEVD-AMC) activity was then performed. The numbers represent relative AMC fluorescence in each sample compared to the value obtained with untreated Jurkat cells incubated for 24 hours, set at 1. Standard deviation values are also shown.
Figure 6G:
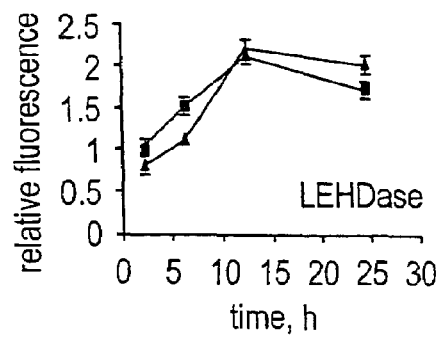
FIG. 6G is a graph showing the time course of caspase activation in Jurkat cells, as assayed using a QuantiPak kit (Biomol). The cells were treated with 100 μM of BH3I-1 (triangles) or 50 μM of BH3I-2 (squares) for 2, 6, 12 or 24 hr. A fluorescence based assay of caspase-9 (Ac-LEHD-AMC) activity was then performed. The numbers represent relative AMC fluorescence in each sample compared to the value obtained with untreated Jurkat cells incubated for 24 hours, set at 1. Standard deviation values are also shown.
Figure 6H:
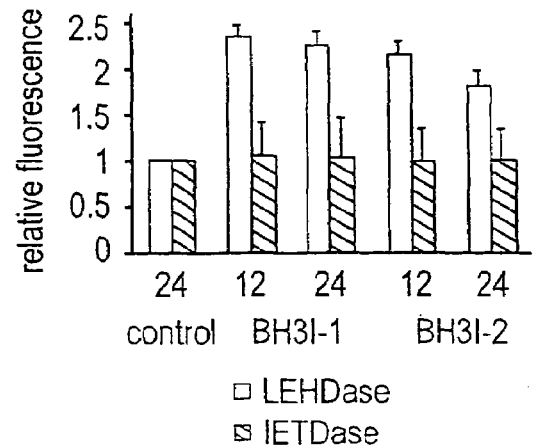
FIG. 6H is a graph showing the comparison of caspase-9 (Ac-LEHD-AMC) (open bars) and caspase-8 (Ac-IETD-AMC) (closed bars) activation 12 and 24 hr after treatment of Jurkat cells with BH3Is.

To evaluate the activation of caspases by BH3Is, the activation of caspases in the presence of these compounds was measured using the preferred caspase-3 and caspase-9 fluorogenic substrates DEVD.amc and LEHD.amc. Treatment of Jurkat cells with either BH3I-1 or BH3I-2 resulted in an increase in caspase-3-like (FIG. 6F) and caspase-9-like (FIG. 6G) activities. Activation of both caspases followed an essentially identical time course and reached a maximum 12 hours after addition of the BH3I. If BH3Is induce apoptosis through a mitochondrial pathway, caspase-9 should be activated before caspase-8, since the latter is a mediator of the death receptor pathway at the plasma membrane (Cryns et al., Genes Dev. 12:1551-70, 1998 [published erratum appears in Genes Dev. 13:371, 1999]). Therefore, the levels of caspase-9 and caspase-8 activity were compared by measuring LEHD.amc/IETD.amc cleavage activities. The BH3Is failed to induce the activation of caspase-8-like activity after 12 and 24 hrs of treatment when caspase-9-like activity was elevated (FIG. 6H). These data indicate that BH3Is induce the activation of caspases in the mitochondrial pathway.

The conditions under which cell death occurs in the presence of BH3Is were further evaluated. HeLa cells were pretreated with zVAD-fmk (100 µM) for 1 hour. The purpose of such a treatment was to inhibit the intracellular pathways mediating cell death by apoptosis. Each of the chemical compounds BH3I-1, BH3I-1', or BH3I-2 was then added to the media of the cells of three separate samples. After 48 or 72 hours of exposure of the cells to zVAD-fmk and the chemical compound, the level of cell death was measured for each sample, by measuring cellular ATP levels. In each cell sample, the cellular ATP levels decreased relative to samples that received no chemical compounds from the ChemBridge library. These results indicated that the above-identified compounds exert their effects on cell death not only through apoptosis, but also through necrosis.

EXAMPLE 5

Small Molecules That Inhibit Interaction Between a Bak Polypeptide and a Bcl-xL/GST Fusion Protein Also Increase Cell Death in Cells Resistant to Cell Death In another study, HeLa cells that stably overexpress human BCL-XL, and are therefore more resistant to cell death, were pretreated with zVAD-fmk (100 µM) for 1 hour, as described above. Each of the chemical compounds BH3I-1, BH3I-1', and BH3I-2 from the ChemBridge library was then added to the media of the cells of three separate samples. After 48 or 72 hours of exposure of the cells to zVAD-fmk and the chemical compound, the level of cell death was measured for each sample, by measuring cellular ATP levels. In each cell sample, the cellular ATP levels decreased relative to samples that received no chemical compounds from the ChemBridge library. These results demonstrate that cells which are resistant to cell death undergo death in response to BH3I-1, BH3I-1', and BH3I-2.

EXAMPLE 6

BH3Is Induce Apoptosis Through Disruption of the BH3 Domain Interaction

Figure 7A:
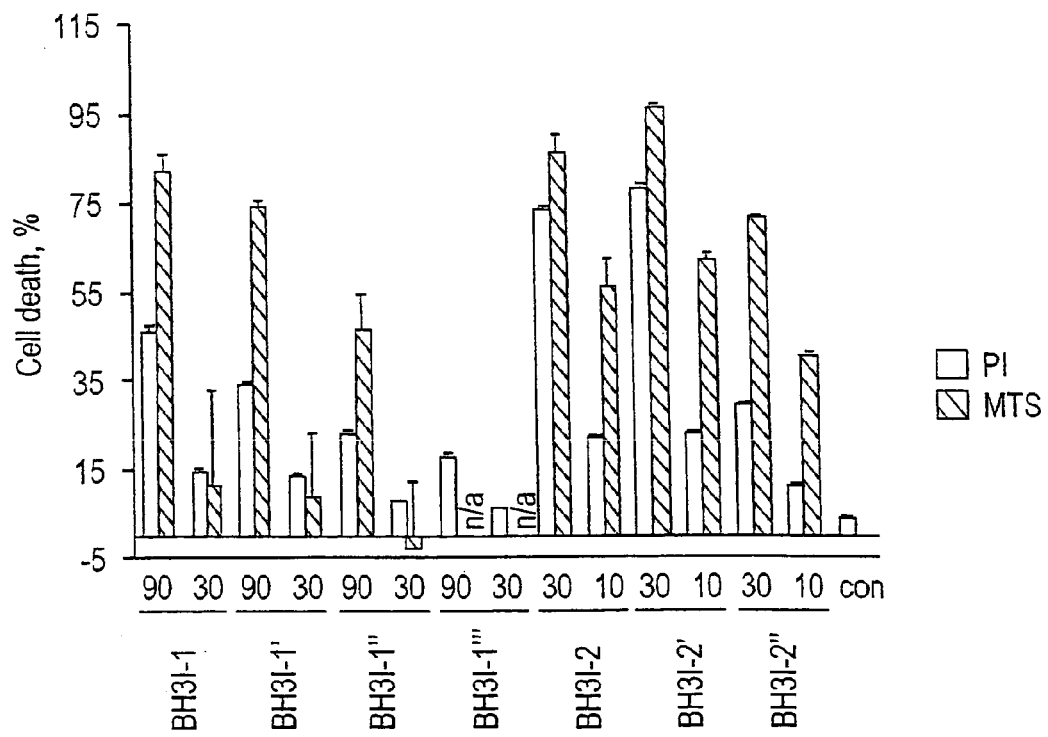
FIG. 7A is a graph showing the effects of BH3Is on cell death, measured by an MTS assay and propidium iodide staining.
Figure 7B:
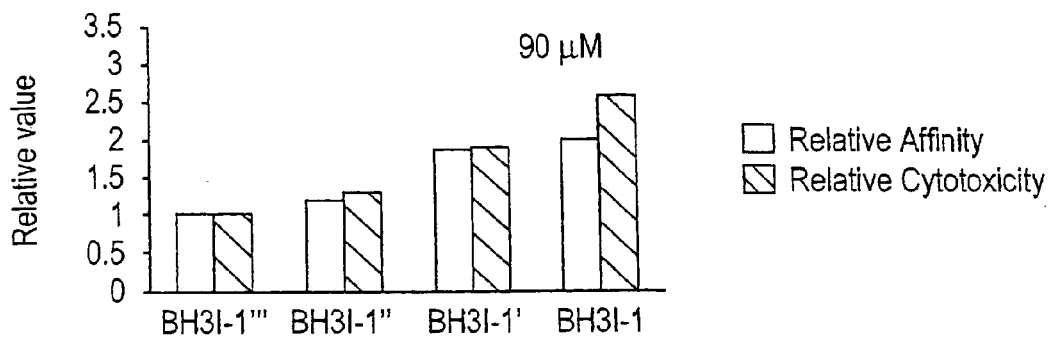
FIG. 7B is a graph showing the effect of the relative cytotoxicities of BH3I-1s, determined by propidium iodide staining, and their binding affinities.
Figure 7C:
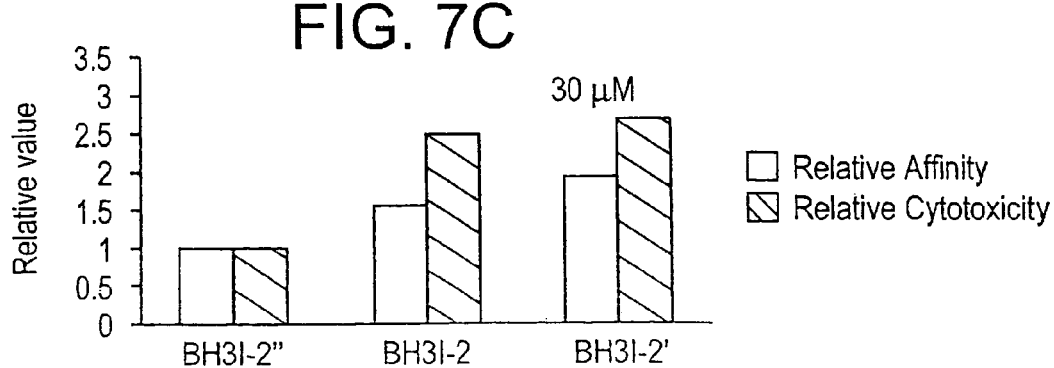
FIG. 7C is a graph showing the effect of the relative cytotoxicities of BH3I-2s, determined by propidium iodide staining, and their binding affinities.

Since BH3Is induce apoptosis, their mode of action, for example, through disruption of BH3 domain interactions, was investigated next. If apoptosis induced by a BH3I is BH3-dependent, then cytotoxicity should correlate with the compound's ability to disrupt BH3 domain interactions in vitro. To examine this possibility, Jurkat cells were treated with the BH3 Is and the occurrence of cell death was assayed by the MTS assay and propidium iodide (PI) uptake (FIG. 7A). The cytotoxicity of BH3-Is followed the order of BH3I-2'>BH3I-2>BH3I-2">BH3I-1>BH3I-1'>BH3I-1">BH3I-1''' which paralleled the order of their Ki values determined using in vitro Bcl-xL binding assays (FIGS. 7B and 7C). Similar data were obtained using a trypan blue exclusion assay. These results suggest that the ability to inhibit the BH3 domain interaction is critical for BH3I-mediated induction of cell death.

The effect of the BH3Is on the disruption of the heterodimerization of Bcl-2 family proteins in vivo was next determined. Dimerization of Bcl-2 in immunoprecipitation experiments may represent post-lysis events induced by detergents (Hsu et al., J. Biol. Chem. 272:13829-34, 1997). Therefore, these studies focused on assaying the Bcl-xL dimerization status in intact cells. Recently, the interaction between Bax and Bcl-2 has been studied in intact living cells by fluorescent resonance energy transfer measurements between GFP fusion proteins (Mahajan et al., Nat. Biotechnol. 16:547-52, 1998). This approach was used to monitor the effects of BH3Is on Bcl-xL/Bax heterodimerization in intact cells.

293 cells were transfected with Bcl-xL-CFP and Bax-YFP expression vectors using Lipofectamine Plus (Gibco) or TransLT-1 (PanVera) and 24 hr later were treated with BH3Is. Cells were harvested in PBS supplemented with BH3Is, and fluorescence was determined using a C-60 fluorimeter (PTI) or a Wallac platereader. Fluorescence in the samples separately overexpressing Bax and Bcl-xL was added together and used to estimate the FRET value in the absence of dimerization. The extent of FRET between CFP and YFP was determined as a ratio of fluorescence at 527 nm vs. 475 nm after excitation at 433 nm.

Figure 8A:
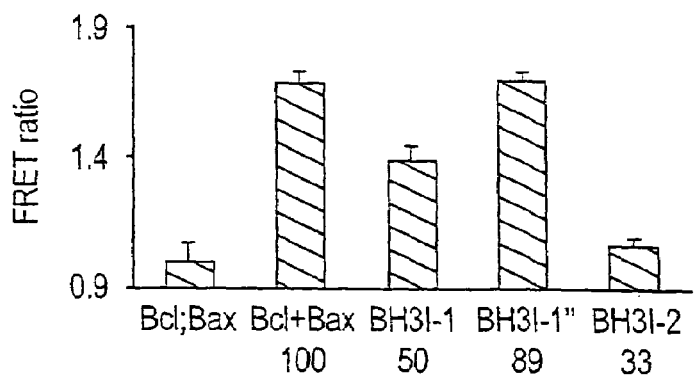
FIG. 8A is a graph showing the FRET ratio of Bax/Bcl-xL binding. The values represent FRET ratios normalized relative to the FRET value obtained for the separate expression of Bax-YFP and Bcl-xL-CFP, which was set at 1.0. The index of cell viability, normalized relative to the DMSO treated Bcl-xL-CFP and Bax-YFP co-transfected cells, which was set as 100% viability, is shown.
Figure 8B:
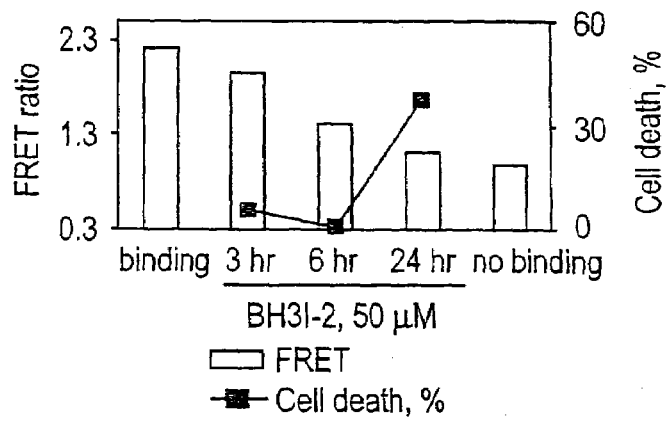
FIG. 8B is a graph showing a time course of changes in FRET values and cell death, measured by propidium iodide staining, induced by BH3I-2 at 50 μM.

Co-transfection of Bax-YFP and Bcl-xL-CFP resulted in an increase in the relative FRET ratio from 1.0 (when two proteins are expressed separately) to 1.7 (FIG. 8A), indicative of Bax/Bcl-xL interactions in the cells. Addition of BH3Is resulted in changes in the FRET ratio consistent with the in vitro activities of the compounds: BH3I-2>BH3I-1>BH3I-1". YFP 513/527 nm fluorescence was not affected by FRET and could serve as an accurate indicator of the Bax-YFP levels and a rough index of cell death. The relative effects on YFP fluorescence reduction also followed the order of BH3I-2>BH3I-I>BH3I-1" (FIG. 8A). These results are consistent with previous cell viability studies and demonstrate that the ability of the BH3Is to disrupt Bax/Bcl-xL interactions in intact cells directly correlates with cytotoxicity in the same samples. Time course experiments, which demonstrated that disruption of FRET preceded cell death, were also performed (FIG. 8B).

Figure 8C:
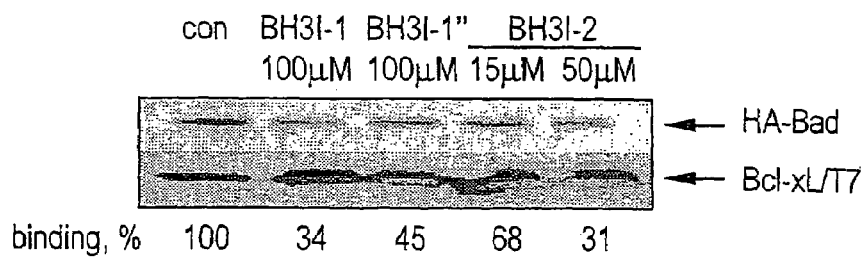
FIG. 8C is an images of a the expression of Bad and Bcl-xL in 293 cells co-transfected with HA-Bad and Bcl-xL-T7. After 48 hr, cells were harvested and isolated mitochondria were treated with BH3Is for 2 hrs. Following treatment, mitochondria were pelleted by centrifugation and subjected to Western blot analysis using anti-HA and anti-T 7 antibodies.
Figure 8D:
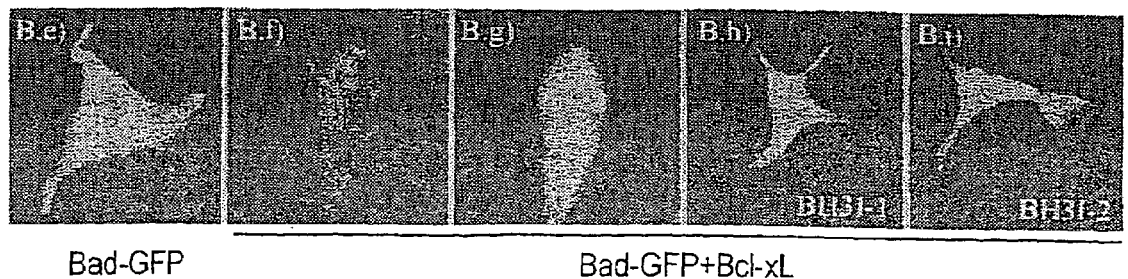
FIG. 8D is a series of images of cells showing the effects of BH3Is on the localization of Bad.

Bad is a pro-apoptotic member of the Bcl-2 family, whose apoptosis-promoting activity and mitochondrial targeting depends on heterodimerization with anti-apoptotic Bcl-2 family members (Zha et al., Cell 87, 619-28, 1996). To examine the effects of BH3Is on Bad localization, BSC-1 cells were transfected with 5 µg of Bad-GFP expression vector alone (FIG. 8D, panels 1 and 5) or were co-transfected with 5 µg of Bad-GFP and 5 µg of Bcl-xL-T7 (FIG. 8D, panels 2-5). Twenty four hours after transfection, cells were treated with BH3I-1 (100 µM; FIG. 8D, panel 4) or BH3I-2 (50 µM; FIG. 8D, panel 5) for 6 hr. The GFP signal in the fixed cells is shown in FIG. 8D, panels 1 and 3-5. In order to determine mitochondrial localization, cells were pre-stained with MitoTracker Red CMXRos for 30 min prior to fixation (FIG. 8D, panel 2). All cells in this study were pretreated with 100 µM zVAD to decrease the detrimental effects of overexpression of proapoptotic Bcl-2 proteins on cell viability.

Transfection of the cells with the Bad expression vector resulted in the predominantly cytoplasmic localization of Bad (FIG. 8D, panel 1), whereas co-transfection with Bcl-xL resulted in the mitochondrial localization of Bad (FIG. 8D, panel 2 and 3). BH3Is disrupted the mitochondrial association of Bad, but not Bcl-xL, after in vitro treatment of the mitochondria isolated from 293 cells co-transfected with Bad and Bcl-xL (FIG. 8C). The relative activities of the BH3Is in this assay (BH3I-2>BH3I-1>BH3I-1") were consistent with the previous results. Treatment of cells with either BH3I-1 or BH3I-2 resulted in an increase in the number of cells with the cytosolic redistributed Bad-GFP. Quantitation of cells with mitochondrial versus cytosolic localization of Bad-GFP indicated that BH3I-1 and BH3I-2 efficiently disrupted mitochondrial targeting and heterodimerization of Bad-GFP with either Bcl-2 or Bcl-xL in intact cells (FIG. 8D). Again, the order of the activities in these assays was BH3I-2>BH3I-1>BH3I-1". No cell death was detectable at the time of measurement, suggesting that in this system, disruption of BH3 interactions also precedes cell death.

Figure 9A:
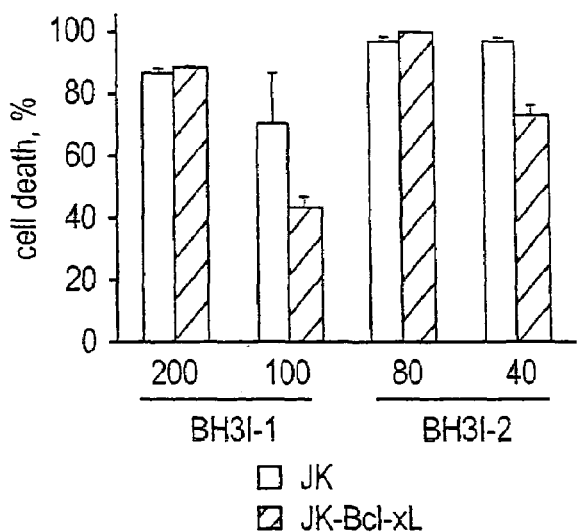
FIG. 9A is a graph showing the attenuation of BH3I cytotoxicity by Bcl-xL, as determined by an MTS assay, in Jurkat cells or in Jurkat cells overexpressing Bcl-xL.
Figure 9B:
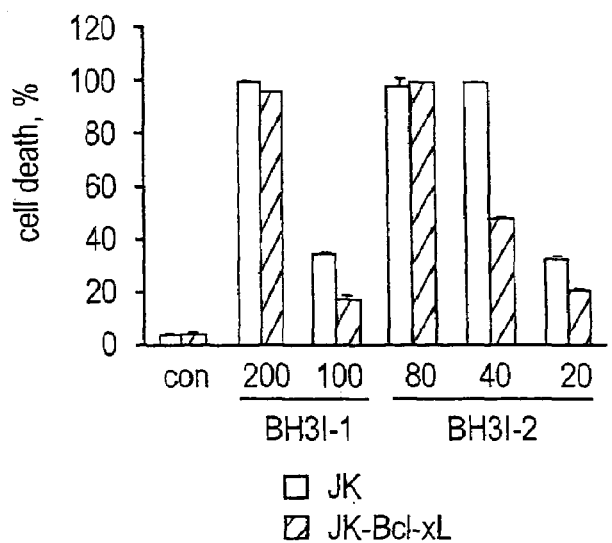
FIG. 9B is a graph showing the attenuation of BH3I cytotoxicity by Bcl-xL, as determined by propidium iodide staining, in Jurkat cells or in Jurkat cell overexpressing Bcl-xL.
Figure 9D:
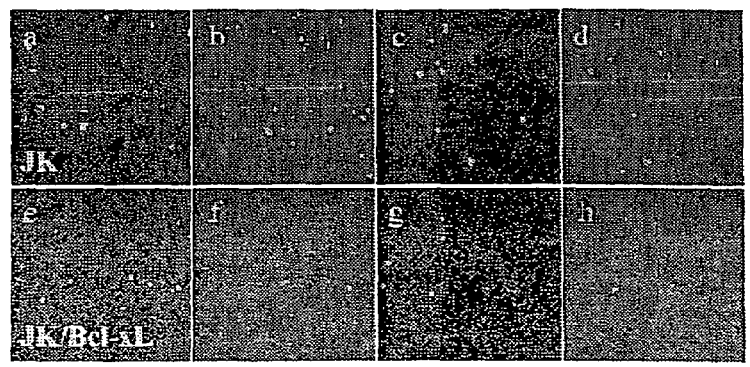
FIG. 9D is a series of images showing caspase activation in Jurkat cells or in Jurkat cells overexpressing Bcl-xL and treated with BH3Is.
Figure 9C:
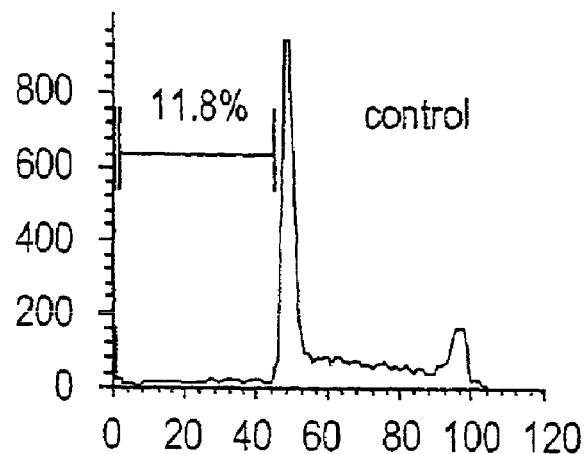
FIG. 9C is a series of graphs showing DNA fragmentation analysis of Jurkat cells overexpressing Bcl-xL and treated with BH3Is.
Figure 9C:
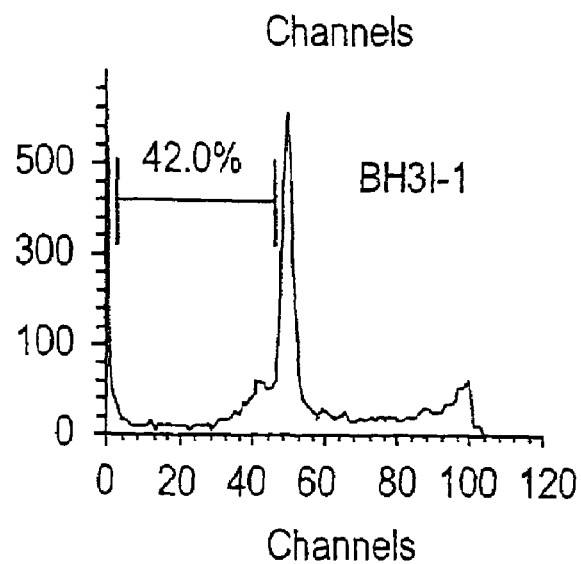
Figure 9C:
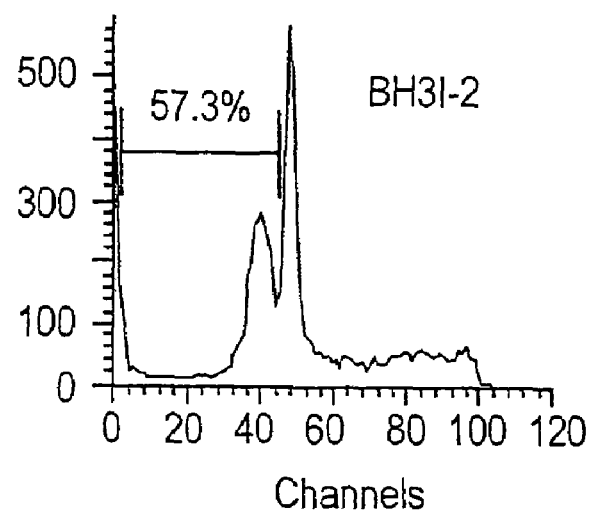

If BH3Is act through inhibiting the function of anti-apoptotic members of Bcl-2 family, overexpression of Bcl-xL should provide protection against BH3Is, which can be overcome by increased amount of BH3Is. Furthermore, Bcl-xL overexpressing cells. should still undergo apoptosis when treated with a high enough dose of a BH3I to overcome the protection by Bcl-xL. To test this theory, Jurkat/Bcl-xL cells were treated with BH3I-1 and BH3I-2 for 48 hr. Cell death was determined using the MTS assay (FIG. 9A) or PI staining (FIG. 9B). Overexpression of Bcl-xL provided protection for Jurkat cells from lower doses of BH3Is (up to 40 µM of BH3I-2 and up to 100 µM of BH3I-1). Overexpression of Bcl-xL, however, gave no protection after treatment with 80 µM of BH3I-2 or 200 µM of BH3I-1. BH3I treatment (100 µM of BH3I-1 or 30 µM of BH3I-2) induced the appearance of sub-GI DNA, which is also indicative of apoptosis (FIG. 9C). To determine if caspases were activated in Jurkat/Bcl-xL cells treated with high doses of BH3Is, indicating that cells were undergoing apoptosis rather than necrosis, the cell were stained with FAM-VAD-fik, which binds to the active caspases and allows visualization of caspase activation in intact cells (FIG. 9D). Caspases were activated in Hoechst-positive dying cells following treatment with high doses of BH3Is. No Hoechst/caspase positive cells were seen in untreated control cells.

Figure 9E:
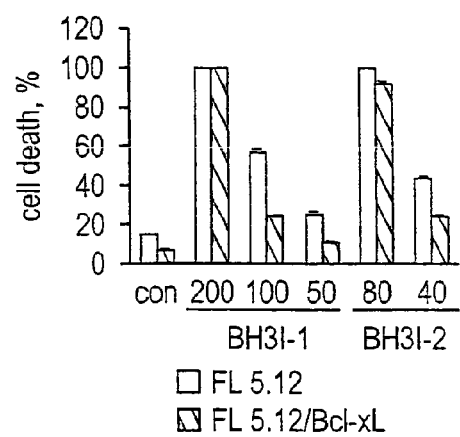
FIG. 9E is a graph showing the attenuation of cell death in FL 5.12 cells by Bcl-xL overexpression in cells treated with BH3Is.
Figure 9F:
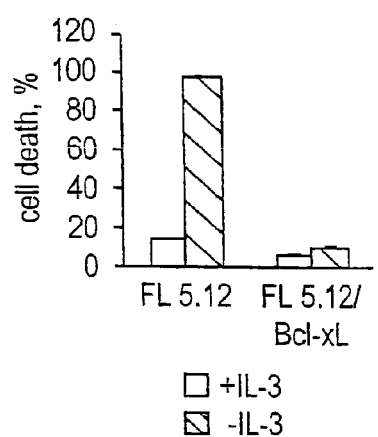
FIG. 9F is a graph showing the attenuation of cell death in FL 5.12 cells by Bcl-xL overexpression in cells subjected to IL-3 deprivation.
Figure 9G:
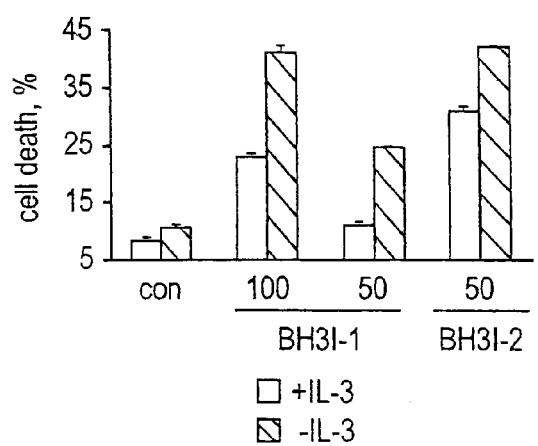
FIG. 9G is a graph showing the inactivation of the antiapoptotic activity of Bcl-xL by BH3Is in FL 5.12 cells, as determined by propidium iodide staining.
Figure 9H:
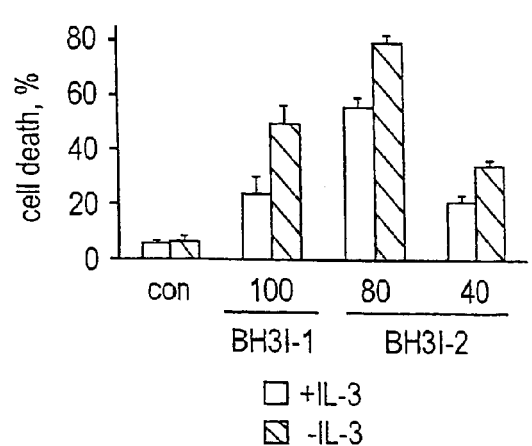
FIG. 9H is a graph showing the inactivation of the antiapoptotic activity of Bcl-xL by BH3Is in FL 5.12 cells, as determined by counting cells with activated caspases.

In an additional study of the attenuation of cell death by Bcl-xL overexpression and treatment with BH3Is, FL5.12 cells undergo apoptosis in response to IL-3 deprivation, and this cell death is efficiently blocked by overexpression of Bcl-xL (Vander Heiden et al., Mol. Cell. 3:159-67, 1999) (FIG. 9F). This effect could be overcome by a higher dose of BH3Is (FIG. 9E). Inactivation of Bcl-xL by BH3Is in FL5.12/Bcl-xL cells was detected as an increase in cell death following IL-3 deprivation. The cytotoxicity of BH3I-1 and BH3I-2 significantly increased upon IL-3 deprivation of the Bcl-xL overexpressing cells, whereas IL-3 deprivation alone did not induce significant cell death (FIG. 9G). Moreover, staining cells with FAM-VAD-fmk revealed increased caspase activation induced by combined treatment with BH3Is and IL-3 deprivation in Bcl-xL/FL5.12 cells (FIG. 9H), demonstrating an enhancement in apoptosis in these cells in response to Bcl-xL inactivation.

Figure 10A:
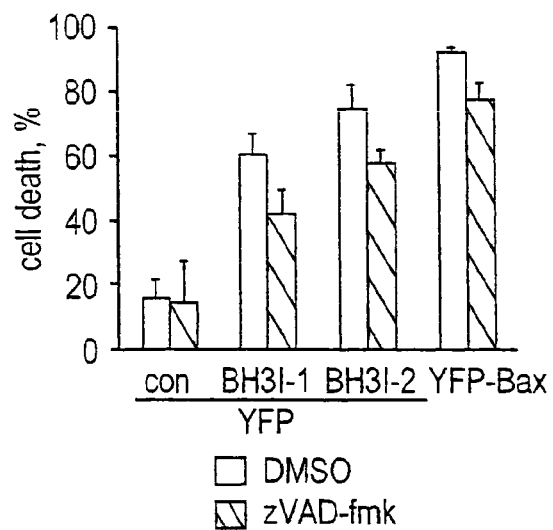
FIG. 10A is a graph showing the comparison of BH3Is and Bax induced cell death. HeLa cells were transfected with YFP-Bax and pEYFP-C 1 for 48 hr in the absence (open bars) or presence (closed bars) of 100 μM zVAD-fmk. YFP transfected cells were also treated with BH3I-1 (100 μM) or BH3I-2 (50 μM) for 48 hours. Cell viability was determined by propidium iodide (PI) staining and microscopic examination of PI/YFP positive cells. Numbers represent the percentage of PI positive cells in the YFP positive population. The values of standard deviation are also shown.
Figure 10B:
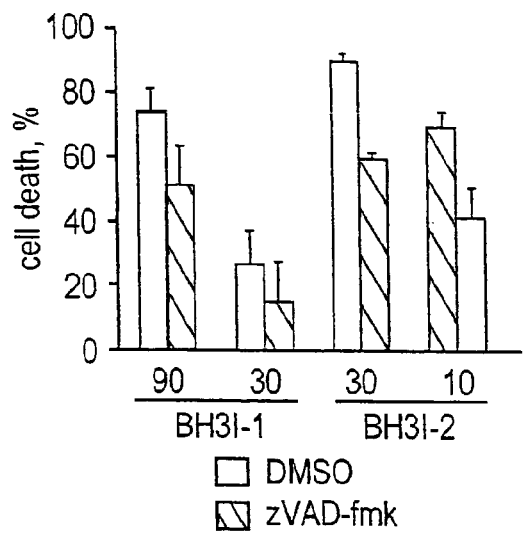
FIG. 10B is a graph showing the attenuation of BH3Is' cytotoxicities by the pan-caspase inhibitor zVAD-fmk. Jurkat cells were treated with BH3I-1 or BH3I-2 in the presence (open bars) or absence (closed bars) of 100 µM zVAD-fmk (Alexis) for 48 hr. Cell death was determined using an MTS assay. Numbers represent the percentages of cell death, normalized relative to a DMSO treated control, which was set at 100% viability. Standard deviation values are also shown.

Finally, if inhibition of the BH3 domain interaction results in the release of pro-apoptotic members of Bcl-2 family, the pro-apoptotic activity of BH3Is should mimic that of pro-apoptotic members of the Bcl-2 family. Therefore, the pro-apoptotic activity of the BH3Is was compared with that of Bax. Cell death induced by either BH3I treatment of HeLa cells or by transfection with Bax was only partially dependent upon caspase activity (FIG. 10A). MTS (FIG. 10B) and PI (FIG. 10A) exclusion assays of BH3Is/zVAD treated Jurkat cells confirmed this conclusion.

Figure 10C:
FIG. 10C is a set of images of cells showing that nuclear fragmentation, but not cytochrome c release, induced by BH3Is, requires caspases. HeLa cells were treated with 100 µM BH3I-1 and 100 µM zVAD-fmk for 48 hr and stained with Hoechst (a) or cytochrome c antibody (b). Arrows indicate the positions of the dying cells.

In order to further characterize the role of caspases in BH3I-induced apoptosis, HeLa cells that had been treated with BH3Is in the presence of zVAD-fmk were stained with Hoechst dye and anti-cytochrome c antibody. Addition of zVAD-fmk completely protected cells from BH3I-induced nuclear fragmentation, but not from nuclear condensation or cytochrome c release induced by BH3I-1 (compare FIG. 10C and FIG. 6D) and BH3I-2. This conclusion was confirmed by subG1 analysis showing that zVAD-fmk prevented the appearance of fragmented DNA in cells treated with BH3Is (FIGS. 10D1-10D6). Therefore, although BH3Is induce some events that require caspase activation, similar to Bax-induced cell death, eventual cellular demise is only partially dependent upon caspase activity (Xiang et al., Proc. Natl. Acad. Sci. USA 93:14559-63,1996; and Gross et al., EMBO J. 17:3878-85, 1998). Thus, BH3Is induce apoptosis by disrupting the BH3 domain interaction between pro- and anti-apoptotic members of the Bcl-2 family.

EXAMPLE 7

Neither Bak BH3 Peptide nor BH3Is Affect the Pore Formation by Bcl-xL

Bcl-xL forms membrane pores, and the formation of these pores may play a role in Bcl-xL's ability to regulate apoptosis. Thus, the effects of the BH3Is on pore formation by Bcl-xL were tested (Minn, et al., Nature 385:353-7, 1997; Schendel et al., Proc. Natl. Acad. Sci. USA 94:5113-8, 1997; Minn et al., EMBO J. 18:632-43,1999; and Matsuyama et al., J. Biol. Chem. 273:30995-1001, 1998). Liposomes containing 20 mM of 5,6-carboxyfluorescein were prepared as previously described (Antonsson, et al., Science 277:370-2, 1997). For Bcl-xL pore formation 5 µM Bcl-xL-His$_6$ was preincubated with BH3I-2 or Bak BH3 peptide in 50 µl of 5 mM sodium citrate, 150 mM NaCl, pH 4.0 buffer for 10 min at 25° C., followed by addition of 5 µl of undiluted liposomes. Prior to determination of the fluorescence pH was adjusted by adding 10 µl of 1.5 M Tris-HCl, pH 7.5. Neither BH3Is nor BH3 peptide affected Bcl-xL-mediated release of carboxyfluorescein encapsulated in artificial liposomes. This result suggests that Bcl-xL pore formation is independent of BH3-mediated homodimerization, and that the pro-apoptotic activity of BH3Is reflects a critical role of BH3-dependent heterodimerization in mediating cell survival.

EXAMPLE 8

BH3Is Interact with the BH3-peptide Binding Pocket of Bcl-xL

NMR titration was used to examine whether BH3I interacts with the binding pocket of Bcl-xL in a manner similar to Bak BH3 peptide (Hajduk et al., Science 278:497-499, 1997).

First, the changes in 2D $^{15}$N/$^1$H heteronuclear single quantum correlation spectrum (HSQC) of $^{15}$N-labeled Bcl-xL upon addition of the Bak BH3 peptide were analyzed. Addition of Bak BH3 peptide primarily affected residues in the BH1-BH3 hydrophobic cleft, especially residues on the BH1/BH2 interface, consistent with the published structure of the Bak/Bcl-xL complex (Sattler et al., Science 275:983-6, 1997).

Next, changes in Bcl-xL structure upon addition of increasing amounts of BH3Is were determined. Each of the BH3Is induced significant changes in the Bcl-xL structure. The compounds targeted the hydrophobic cleft formed by the BH1, BH2, and BH3 domains on the surface of the Bcl-xL protein, and primarily bound to the area formed by BH1 and BH2 domains. The NMR data also indicated that BH3I-2s display slower dissociation rates than BH3I-1s, judged by the predominantly intermediate exchange kinetics of BH3I-2s binding compared to the fast exchange shown by BH3I-1s.

Since BH3I-1 differs from BH3I-1" by a single substitution, the changes induced by these chemicals in the $^{15}$N/$^1$H HSQC spectra of Bcl-xL were compared (Hajduk et al., J. Med. Chem. 42:2315-7, 1999). The primary area differentially affected by BH3I-1 and BH3I-1" was in the middle of the BH2 domain (residues N100, G102, I104, A106, F110, G111, G112). The only other differentially-affected residue was R55, which is positioned in the BH3 domain. Similar comparative analysis of BH3I-2 and BH3I-2' resulted in the mapping of A164, A165, R168, located C-terminal to the BH1 domain, and F110 in the BH2 domain. This suggests that BH3I-2s target a more upstream part of the Bcl-xL hydrophobic groove than that which is targeted by BH3I1-s.

Additionally, the magnetization transfer between the benzene ring protons of BH3I-1 and the amide protons of Y65 and F107 in a Nuclear Overhauser Effect (NOE) spectrum was observed, indicative of direct contact between BH3I-1 and these residues. Interestingly, residue F107, as well as residues F110, A164, A165, and R168 (residues identified in differential mapping analysis) are buried in the structure of free Bcl-xL, but are surface exposed in the structure of Bcl-xL/Bak complex (Muchmore et al., Nature 381:335-41, 1996; and Sattler et al., Science 275:983-6,1997). In this complex Y65, F107, and F100 form direct contacts with the side-chain of the leucine residue of Bak BH3 peptide, which is essential for binding. This observation suggests that upon binding of BH3I-1, Bcl-xL undergoes a conformational change similar to that induced by the Bak BH3 peptide.

Overall, the results of the above NMR studies demonstrated that BH3Is target the hydrophobic cleft on the surface of Bcl-xL, which is a docking site for the BH3 domain of Bak that mediates the dimerization of Bcl-2 family members. Binding of BH3Is to the hydrophobic pocket of Bcl-xL affects the conformation of Bcl-xL in a fashion similar to that of the Bak BH3 peptide binding. This suggests a similarity between the modes of action of the BH3Is and the Bak BH3 peptide.

EXAMPLE 9

Structural Derivatives of Small Molecules that Increase Cell Death

One or more of the following modifications of the small molecules that increase cell death may be made and evaluated for their efficacy in increasing cell death.

Figure 11:
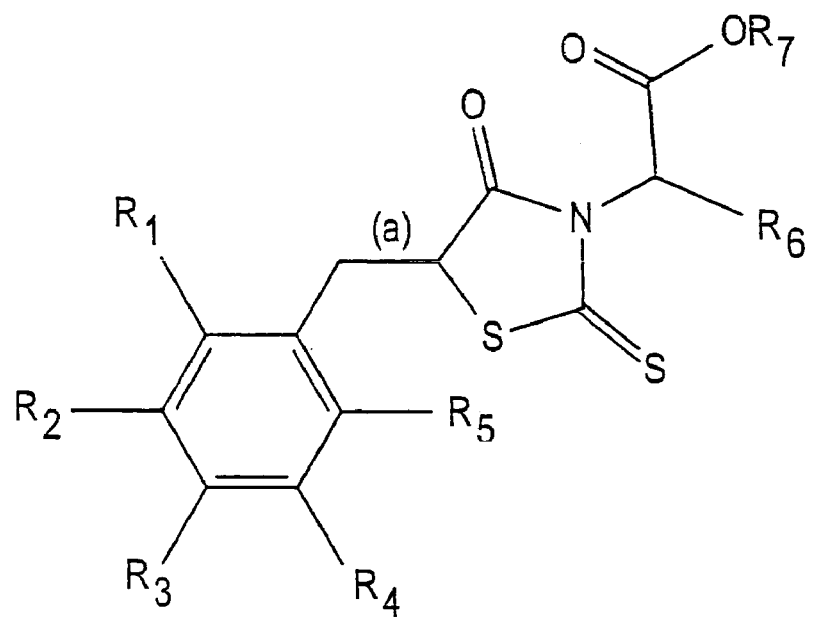
FIG. 11 is a schematic representation of the chemical structure of a compound used to increase cell death. Each of $R_1$, $R_2$, $R_4$, and $R_5$ is independently selected from the group consisting of hydrogen, alkoxyl, hydroxyl, and halogens; $R_3$ is selected from the group consisting of $N(CH_3)_2$, phenyl, hydroxyl, alkoxyl, and halogens; $R_6$ is selected from the group consisting of $CH(CH_3)_2$, $CH_2CH(CH_3)_2$, $CH(CH_3)CH_2CH_3$, and $CH_3$; $R_7$ is either hydrogen or an alkyl group; and the bond (a) is either a single or double bond.

The chemical compound 275806 (BH3I-1) or 282986 (BH3I-1') may be modified by substituting the valine moiety with a leucine, isoleucine, or alanine moiety; substituting the heterocyclic ring with a benzyl ring (wherein substituents on the central may be in para-, meta-, or ortho-positions); reducing the double bond (bond (a) in FIG. 11) attached to the heterocyclic ring; introducing additional constituents, for example, hydroxyl, alkoxyl, or halogen groups at various positions (for example at each of positions $R_1$, $R_2$, $R_4$, and $R_5$ in FIG. 11) of the benzyl ring; substituting bromine or chlorine (for example, at the $R_3$ position in FIG. 11) with a hydroxyl, alkoxyl, or phenyl group or derivative of a phenyl group; or converting the carboxyl group (for example, the $R_7$ group in FIG. 11) into an ester.

Figure 12:
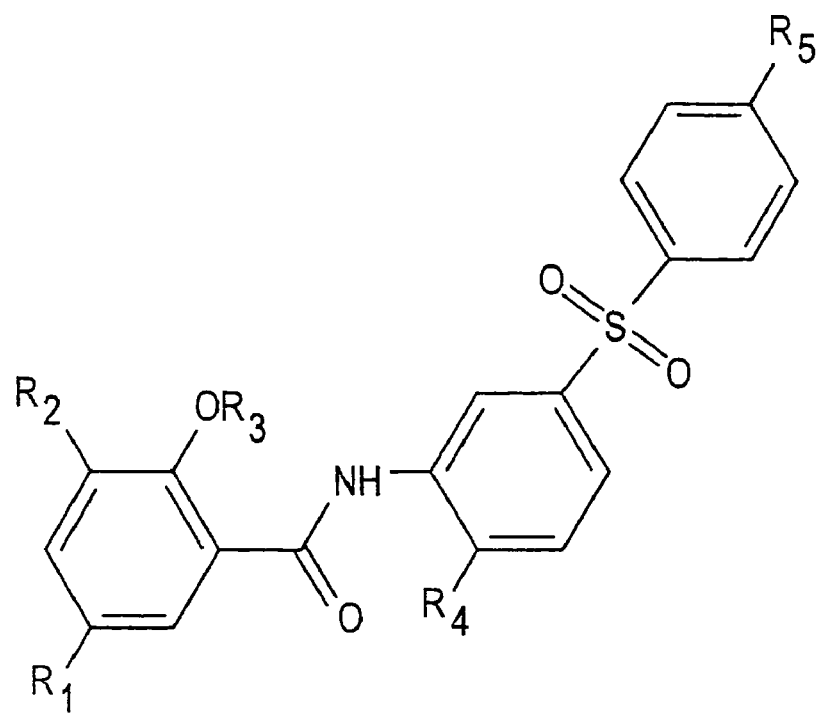
FIG. 12 is a schematic representation of the chemical structure of a compound used to increase cell death. Each of $R_1$, $R_2$, $R_4$, and $R_5$ is, independently, hydrogen, a halogen, or a phenyl group; and $R_3$ is hydrogen or an alkyl group.

The chemical compound 175362 (BH3I-2) may be modified by eliminating various halogen groups (for example each of $R_1$, $R_2$, $R_4$, and $R_5$ in FIG. 12); etherification of the hydroxyl group (for example, $R_3$ in FIG. 12); or substitution of a halide group with a phenyl group, or a derivative of a phenyl group (for example each of $R_1$, $R_2$, $R_4$, and $R_5$ in FIG. 12).

OTHER EMBODIMENTS

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

What is claimed is:

1. A method for increasing cell death, said method comprising the steps of:
   (a) providing a cell predicted to be resistant to cell death, or to be at risk for resisting cell death; and
   (b) contacting said cell with a chemical compound having the formula:

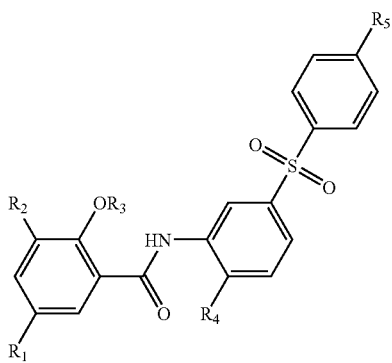

wherein each of $R_1$, $R_2$, $R_4$, and $R_5$ is, independently, hydrogen, a halogen, or a phenyl group; and $R_3$ is hydrogen or an alkyl group.

2. The method of claim 1, wherein
   each of $R_1$, $R_4$, and $R_5$ is chlorine;
   $R_2$ is bromine; and
   $R_3$ is hydrogen.

3. The method of claim 1, wherein
   each of $R_1$, $R_4$, and $R_5$ is chlorine;
   $R_2$ is iodine; and
   $R_3$ is hydrogen.

4. The method of claim 1, wherein
   each of $R_1$ and $R_2$ is iodine;
   each $R_4$ and $R_5$ is chlorine; and
   $R_3$ is hydrogen.

5. The method of claim 1, wherein said compound is substantially pure.

6. The method of claim 1, wherein said compound is in a pharmaceutically acceptable carrier.

7. The method of claim 1, wherein said cell is mammalian.

8. The method of claim 7, wherein said cell is human.

9. The method of claim 7, wherein said cell is a rodent cell.

* * * * *